(12) United States Patent
Dziubla et al.

(10) Patent No.: US 12,102,686 B2
(45) Date of Patent: Oct. 1, 2024

(54) DELIVERY SYSTEMS AND METHODS FOR REACTIVE HYDROXYL-CONTAINING COMPOUNDS

(71) Applicant: University of Kentucky Research Foundation, Lexington, KY (US)

(72) Inventors: Thomas D. Dziubla, Lexington, KY (US); James Zach Hilt, Lexington, KY (US); Carolyn T. Jordan, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/385,854

(22) Filed: Apr. 16, 2019

(65) Prior Publication Data

US 2019/0314512 A1 Oct. 17, 2019

Related U.S. Application Data

(60) Provisional application No. 62/658,063, filed on Apr. 16, 2018.

(51) Int. Cl.
*A61K 47/58* (2017.01)
*A61K 31/12* (2006.01)
*A61K 47/02* (2006.01)
*A61K 47/18* (2017.01)
*A61K 47/69* (2017.01)

(52) U.S. Cl.
CPC .............. *A61K 47/58* (2017.08); *A61K 31/12* (2013.01); *A61K 47/02* (2013.01); *A61K 47/18* (2013.01); *A61K 47/6927* (2017.08)

(58) Field of Classification Search
CPC ........ A61K 31/12; A61K 47/02; A61K 47/18; A61K 47/58; A61K 47/6927
See application file for complete search history.

(56) References Cited

U.S. PATENT DOCUMENTS 8,642,087 B1 * 2/2014 Dziubla ................ C08F 220/06
424/487
2017/0224632 A1 * 8/2017 Shah ......................... A61K 9/19

OTHER PUBLICATIONS

Song et al. Oxidation-Responsive Poly(amino ester)s Containing Arylboronic Ester and Self-Immolative Motif: Synthesis and Degradation Study. Macromolecules 2013, 46, 8416-8425 (Year: 2013).*
Lyu et al. Degradability of Polymers for Implantable Biomedical Devices. Int J Mol Sci. Sep. 2009; 10(9):4033-4065. (Year: 2009).*
Liu et al. Therapeutic Nanocarriers with Hydrogen Peroxide-Triggered Drug Release for Cancer Treatment. Biomacromolecules 2013, 14:1627-1636. (Year: 2013).*
Kamaly et al. Degradable Controlled-Release Polymers and Polymeric Nanoparticles: Mechanisms of Controlling Drug Release. Chem Rev. Feb. 24, 2016; 116(4):2602-2663. (Year: 2016).*
S. Prasad, et al., "Cancer Research and Treatment" Official Journal of Korean Cancer Association 2014, 46, 2-18 10.4143/crt.2014.46.1.2.
Z. M. Malik Al-Rubaei et al., "Effects of Local Curcumin on Oxidative Stress and Total Antioxidant Capacity in vivo Study." Pakistan journal of pharmaceutical sciences, 2014. 17(12): p. 1237-1241.
L. M. Fabbri, et al., in COPD: A Guide to Diagnosis and Clinical Management, ed. by N. A. Hanania, A. Sharafkhaneh, Humana Press, Totowa, N.J., 2011, pp. 1-20.
A. L. Lakes, et al., "Reducible Disulfide Poly(beta-amino ester) Hydrogels for Antioxidant Delivery." Editor, 2017.
K. L. Kozielski, et al., "Methods in molecular biology" (Clifton, N.J.) 2016, 1364, 79-87 10.1007/978-1-4939-3112-5_8.
T.-i. Kim, S. W. Kim, "Reactive and Functional Polymers 2011", 71, 344-349 https://doi.org/10.1016//j.reactfunctpolym.2010.11.016.
Lee, S. H., et al., Advanced healthcare materials 2013, 2, 908-915.
Lakes, A. L., et al., "Reducible Disulfide Poly(beta-amino ester) Hydrogels for Antioxidant Delivery." Editor, 2017.
He, G., et al., "Oxygen free radical involvement in acute lung injury induced by H5N1 virus in mice. Influenza and Other Respiratory Viruses", Influenza Other Respir Viruses, 2013. 7(6): p. 945-953.
Kaur, R. r, et al., "Oxidative stress—implications, source and its prevention" Environmental Science and Pollution Research Int., 2014, 21, 1599-1613.
Ferreira, I. M., et al., "Exhaled nitric oxide and hydrogen peroxide in patients with chronic obstructive pulmonary disease: effects of inhaled beclomethasone", American Journal of Respiratory and Critical Care Medicine, 2001 vol. 164, No. 6, pp. 1012-1015.
Kirkham, P. A. and Barnes, P. J, "Oxidative stress in COPD", Chest 2013, vol. 144, No. 1, pp. 266-273.
Halliwell, B., Clement, M. V., Long, L. H., Hydrogen peroxide in the human body, FEBS Letters 2000, vol. 486, No. 1, pp. 10-13 https://doi.org/10.1016/S0014-5793(00)02197-9.
Van Eeden, S. F., Sin, D. D., Oxidative stress in chronic obstructive pulmonary disease: a lung and systemic process, Canadian Respiratory Journal: Journal of the Canadian Thoracic Society 2013, vol. 20, pp. 27-29.

(Continued)

*Primary Examiner* — Robert A Wax
*Assistant Examiner* — Olga V. Tcherkasskaya
(74) *Attorney, Agent, or Firm* — POLSINELLI PC

(57) ABSTRACT

This invention concerns the incorporation of curcumin into the backbone of a hydrolytically degradable crosslinked hydrogel that utilizes poly(beta amino ester) (PBAE) chemistry to provide a tunable protective network with the ability to release at a controlled rate. Upon the introduction of these microparticle systems in to a free radical generating environment, the constituent amount of curcumin present in solution was improved in comparison to a free curcumin state. From these results, a kinetic rate model was developed to estimate oxidative consumption parameters of curcumin and curcumin monoacrylate and quantify theoretical levels of free radicals present depending on the rate of release of curcumin provided. Modeled curcumin conjugated PBAE microparticles improve translation and overall success in delivering a therapeutic agent that matches levels of oxidative stress.

21 Claims, 15 Drawing Sheets

(56) References Cited

OTHER PUBLICATIONS

Caramori, G., et al., "Role of transcription factors in the pathogenesis of asthma and COPD" Cell Communication & Adhesion, 2013, vol. 20, pp. 21-40.
Barnes, P. J., The cytokine network in chronic obstructive pulmonary disease, American Journal of Respiratory Cell and Molecular Biology 2009, vol. 41, pp. 631-638.
Moghaddam, S. J., et al., Curcumin inhibits COPD-like airway inflammation and lung cancer progression in mice, Carcinogenesis 2009, vol. 30, pp. 1949-1956.
Lee, S. H., et al., Current Progress in Reactive Oxygen Species (ROS)-Responsive Materials for Biomedical Applications, Advanced healthcare materials 2013, vol. 2, pp. 908-915.
Lee, D., et al., Hydrogen peroxide-responsive copolyoxalate nanoparticles for detection and therapy of ischemia-reperfusion injury, Journal of controlled release: official journal of the Controlled Release Society 2013, vol. 172, pp. 1102-1110.
Cui, Y., et al., Facile Synthesis of H2O2-Cleavable Poly(esteramide)s by Passerini Multicomponent Polymerization, ACS Macro Letters 2017, vol. 6, No. 1, pp. 11-15.
Biswal, D. et al., A single-step polymerization method for poly(β-amino ester) biodegradable hydrogels, Polymer vol. 52, Issue 26, Dec. 13, 2011, pp. 5985-5992, https://doi.org/10.1016/j.polymer.2011.10.058.
Wattamwar, P. P., et al., Synthesis and characterization of poly(antioxidant β-amino esters) for controlled release of polyphenolic antioxidants, Acta biomaterialia 2012, vol. 8, No. 7, pp. 2529-2537.
Patil, V. S., et al., Static and dynamic properties of biodegradable poly(antioxidant β-amino ester) networks based on incorporation of curcumin multiacrylate, Polymer, vol. 75, Sep. 28, 2015, pp. 88-96. http://dx.doi.org/10.1016/j.polymer.2015.08.034.
Lakes, A. L., et al., "Reducible Disulfide Poly(beta-amino ester) Hydrogels for Antioxidant Delivery." ACTA Biomaterialia,vol. 68, Mar. 1, 2018, pp. 178-189.
Gupta, P., et al, Controlled curcumin release via conjugation into PBAE nanogels enhances mitochondrial protection against oxidative stress, International Journal of Pharmaceutics 2016, vol. 511, No. 2, pp. 1012-1021; http://dx.doi.org/10.1016/j.ijpharm.2016.07.071.
Gupta, P., et al., "Quercetin conjugated poly(β-amino esters) nanogels for the treatment of cellular oxidative stress", Acta Biomaterialia, vol. 27, Nov. 2015, pp. 194-204, http://dx.doi.org/10.1016/j.actbio.2015.08.039.
Lynn, D. M., et al., Degradable Poly(β-amino esters): Synthesis, Characterization, and Self-Assembly with Plasmid DNA, Journal of the American Chemical Society, 2000, vol. 122, pp. 10761-10768.
Kim, T., Kim, Kim, S.W. , "Bioreducible polymers for gene delivery", Reactive and Functional Polymers, vol. 71, Issue 3, Mar. 2011, pp. 344-34; https://doi.org/10.1016//j.reactfunctpolym.2010.11.016.
Borra, S.K., et al., Antioxidant and free radical scavenging activity of curcumin determined by using different in vitro and ex vivo models, Journal of Medicinal Plants Research, 2013, vol. 7, No. 36, pp. 2680-2690.
Gupta et al., "Chapter One—A Free Radical Primer, in Oxidative Stress and Biomaterials, T. Dziubla and D.A. Butterfield", Editors. 2016, Academic Press. p. 1-33.
Redding, S. W., "Cancer therapy-related oral mucositis." Journal of dental education, 2005. 69(8): p. 919-929.
Conner et al., "Inflammation, free radicals, and antioxidants." Nutrition. 12(4): p. 274-277.
He, G., et al., "Oxygen free radical involvement in acute lung injury induced by H5N1 virus in mice. Influenza and Other Respiratory Viruses", 2013. 7(6): p. 945-953.
Zweier et al., "The role of oxidants and free radicals in reperfusion injury." Cardiovascular research, 2006. 70(2): p. 181-190.
Lalla et al., "Management of oral mucositis in patients who have cancer." Dental Clinics of North America, 2008. 52(1): p. 61-77.

Volpato, et al., "Radiation therapy and chemotherapy-induced oral mucositis." Revista Brasileira de Otorrinolaringologia, 2007. 73(4): p. 562-568.
Biswal, B. M., "Current Trends in the Management of Oral Mucositis Related to Cancer Treatment." The Malaysian Journal of Medical Sciences: MJMS, 2008. 15(3): p. 4-13.
Ortiz, F., et al., "Melatonin blunts the mitochondrial/NLRP3 connection and protects against radiation-induced oral mucositis." Journal of Pineal Research, 2015. 58(1): p. 34-49.
Olivera, A., et al., "Inhibition of the NF-κB signaling pathway by the curcumin analog, 3,5-Bis(2-pyridinylmethylidene)-4-piperidone (EF31): anti-inflammatory and anti-cancer properties." International Immunopharmacology, 2012. 12(2): p. 368-377.
Sonis, S., "Oral mucositis." Anti-cancer drugs, 2011. 22(7): p. 607-612.
Spielberger, R., et al., "Palifermin for Oral Mucositis after Intensive Therapy for Hematologic Cancers." New England Journal of Medicine, 2004. 351(25): p. 2590-2598.
Malik Al-Rubaei, Z. M. et al., "Effects of Local Curcumin on Oxidative Stress and Total Antioxidant Capacity in vivo Study." Pakistan journal of pharmaceutical sciences, 2014. 17(12): p. 1237-1241.
Bisson, J., et al., "Can Invalid Bioactives Undermine Natural Product-Based Drug Discovery?" Journal of Medicinal Chemistry, 2016. 59(5): p. 1671-1690.
Rahal, A., et al., "Oxidative Stress, Prooxidants, and Antioxidants: The Interplay." BioMed Research International, 2014. 2014: p. 19.
Patil, et al., "Static and dynamic properties of biodegradable poly(antioxidant β-amino ester) networks based on incorporation of curcumin multiacrylate." Polymer, 2015. 75: p. 88-96.
Wattamwar, P. P., et al., "Synthesis and characterization of poly (antioxidant β-amino esters) for controlled release of polyphenolic antioxidants." Acta biomaterialia, 2012. 8(7): p. 2529-2537.
Gupta, P., et al., "Controlled curcumin release via conjugation into PBAE nanogels enhances mitochondrial protection against oxidative stress." International Journal of Pharmaceutics, 2016. 511(2): p. 1012-1021.
Dash, S., et al., "Kinetic modeling on drug release from controlled drug delivery systems." Acta Pol Pharm, 2010. 67(3): p. 217-23.
Ahsan, H., et al., "Pro-oxidant, anti-oxidant and cleavage activities on DNA of curcumin and its derivatives demethoxycurcumin and bisdemethoxycurcumin." Chemico-biological interactions, 1999. 121(2): p. 161-175.
Patil, V. S., et al., "Curcumin Acrylation for Biological and Environmental Applications." Journal of Natural Products, 2017. 80(7): p. 1964-1971.
Steenken, S. et al., "Oxidation of substituted alkyl radicals by hexachloroiridate(2), hexacyanoferrate(3), and permanganate ions in aqueous solution. Electron transfer versus chlorine transfer from hexachloroiridate(2-) ion." Journal of the American Chemical Society, 1982. 104(5): p. 1244-1248.
Jayaprakasha, G. K., L. et al., "Antioxidant activities of curcumin, demethoxycurcumin and bisdemethoxycurcumin." Food Chemistry, 2006. 98(4): p. 720-724.
Gruber, S. et al., "Tissue reactions to ionizing radiation—Oral mucosa." Mutation Research/Reviews in Mutation Research, 2016. 770: p. 292-298.
McBath, R. A. et al., "Swelling and degradation of hydrogels synthesized with degradable poly (β-amino ester) crosslinkers." Polymer Chemistry, 2010. 1(6): p. 860-865.
Ak, T. et al., "Antioxidant and radical scavenging properties of curcumin." Chemico-biological interactions, 2008. 174(1): p. 27-37.
Fabbri, L. M., et al., in COPD: A Guide to Diagnosis and Clinical Management, ed. by N. A. Hanania, A. Sharafkhaneh, Humana Press, Totowa, N.J., 2011, pp. 1-20.
Ferreira, I. M., et al., "American Journal of Respiratory and Critical Care Medicine 2001", 164, 1012-1015 10.1164/ajrccm.164.6.2012139.
Werber, J., et al., "Analysis of 2,2'-Azobis (2-amidinopropane) dihydrochloride Degradation and Hydrolysis in Aqueous Solutions." Journal of Pharmaceutical Sciences. 100(8): p. 3307-3315.
Zhang, Y., et al., Trigger-Responsive Poly(β-amino ester) Hydrogels, ACS Macro Letters 2014, 3, 693-697.

(56) References Cited

OTHER PUBLICATIONS

Kozielski, K. L., et al., Bioreducible Poly (Beta-Amino Ester) s for Intracellular Delivery of SiRNA, Methods in molecular biology, (Clifton, N.J.) 2016, 1364, 79-87.

* cited by examiner

DELIVERY SYSTEMS AND METHODS FOR REACTIVE HYDROXYL-CONTAINING COMPOUNDS

CROSS REFERENCE TO RELATED APPLICATIONS

This application claims priority to US Provisional Patent Application 62/658,063, filed Apr. 16, 2018, the contents of which are hereby incorporated by reference in their entirety.

GOVERNMENT SUPPORT

This application was made with support from the National Institute of Dental and Craniofacial Institute (NIDCR) under Grant Number R44DE023523. The Government may have certain rights in the invention.

FIELD OF THE INVENTION

The present disclosure generally relates to methods for delivering a reactive hydroxyl-containing compound; a system for delivering a reactive hydroxyl-containing compounds, and kits which comprise a reactive hydroxyl-containing compound.

BACKGROUND OF THE INVENTION

Phenolic and polyphenolic compounds found in the many natural sources have been shown to offer an opportunity for effective as an anti-inflammatory, antioxidant, anti-proliferative and antiangiogenic agents. Indeed empirical data have shown that phenolic and polyphenolic compounds can play a role in inhibiting oxidative stress and other functions at the cytoskeletal level.

Despite proven efficacy and safety, and significant benefits, limited bioavailability of phenolic and polyphenolic compounds provides a major barrier to effectively enable their therapeutic and other practical uses. For example, poor absorption, rapid metabolism, and rapid systemic elimination limit the ability to use phenolic and polyphenolic compounds in therapeutic applications.

To improve the bioavailability of certain phenolic and polyphenolic compounds and increase effectiveness as therapeutics, a number of delivery approaches have been explored including combinations with adjuvants and other agents, conjugation and structural modifications, blocking of metabolic pathways and route modulation. Previous work has demonstrated some improvement in utilizing a multiacrylate system to prolong bioavailability (see, e.g. U.S. Pat. No. 8,642,087 et seq., hereby incorporated by reference in its entirety). A need remains however for methods to effectively deliver a phenol or polyphenol compound to biological tissue and to other targets or surfaces in a wide array of applications.

SUMMARY OF THE INVENTION

Figure 1:
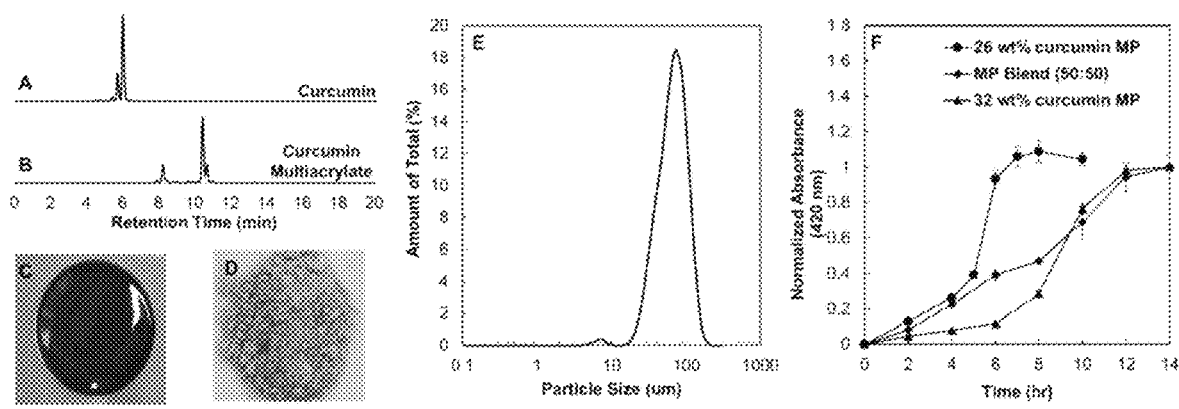
FIGS. 1A-1F shows a characterization of curcumin conjugated PBAE microparticles (MPs). HPLC chromatograms of curcumin (FIG. 1A) and curcumin multiacrylate (FIG. 1B). Curcumin conjugated poly(beta-amino ester) (PBAE) film (FIG. 1C). Cryomilled curcumin conjugated PBAE MPs (FIG. 1D). Distribution of MP size (FIG. 1E). Degradation profiles of 26 wt % (circle), 32 wt % (triangle), and 50:50 blend of 26 and 32 wt % curcumin MP (diamond). (M±SEM, n=3) (FIG. 1F).

In one aspect, disclosed herein, are methods for delivering a reactive hydroxyl-containing compound. In general, the method comprises: a) obtaining a delivery composition comprising a polymer compound comprising a plurality of monomeric portions, each monomeric portion comprising the reactive hydroxyl-containing compound linked to at least two acrylate containing molecules and a plurality of amine linkers, wherein at least one acrylate containing molecule of each monomeric portion is linked by an amine linker to an acrylate molecule of an adjacent monomeric portion to thereby form the polymer; and b) exposing the delivery composition to a trigger which reacts with the polymer to release the reactive hydroxyl-containing compound from the delivery composition.

In another aspect, disclosed herein, is a system for delivering a reactive hydroxyl-containing compound. In general, the system comprises: a) a delivery composition comprising a polymer compound comprising a plurality of monomeric portions each comprising the reactive hydroxyl-containing compound linked to at least two acrylate containing molecules and a plurality of amine linkers, wherein at least one acrylate containing molecule of each monomeric portion is linked by an amine linker to an acrylate containing molecule of an adjacent monomeric portion to thereby forming a polymer; and b) a trigger.

In yet another aspect, disclosed herein, is a kit comprising for delivering a reactive hydroxyl-containing compound. In general, the kit comprises an amount of a delivery composition comprising a polymer compound comprising a plurality of monomeric portions each comprising the reactive hydroxyl-containing compound linked to at least two acrylate containing molecules and a plurality of amine linkers, wherein at least one acrylate containing molecule of each monomeric portion is linked by an amine linker to an acrylate containing molecule of an adjacent monomeric portion to thereby forming a polymer and a trigger. The polymer compound and the amount of the trigger are in separate containers.

Other features and iterations of the invention are described in more detail below.

DETAILED DESCRIPTION OF THE INVENTION

I. Methods for Delivering a Reactive Hydroxyl Compound

One aspect of the present disclosure encompasses methods for delivering a reactive hydroxyl-containing compound. In general, the method comprising: a) obtaining a delivery composition comprising a polymer compound comprising a plurality of monomeric portions, each monomeric portion comprising the reactive hydroxyl-containing compound linked to at least two acrylate containing molecules and a plurality of amine linkers, wherein at least one acrylate containing molecule of each monomeric portion is linked by an amine linker to an acrylate molecule of an adjacent monomeric portion to thereby form the polymer; and b) exposing the delivery composition to a trigger which reacts with the polymer to release the reactive hydroxyl-containing compound from the delivery composition. This method allows for immediate release or timed release of the reactive hydroxyl-containing compound.

a. delivery composition comprising polymeric compounds comprising a reactive hydroxyl-containing molecule.

The delivery composition comprising polymeric compounds comprising a reactive hydroxyl-containing molecule. The polymer compound comprises a plurality of monomeric portions, each monomeric portion comprising the reactive hydroxyl-containing compound linked to at least two acrylate containing molecules and a plurality of amine linkers. The at least one acrylate containing molecule of each monomeric portion is linked by an amine linker to an acrylate molecule of an adjacent monomeric portion to thereby form the polymer. The polymer is linear, branched, or crosslinked.

The monomeric portion can be provided that is comprised of a reactive hydroxyl-containing molecule interposed between a first acrylate molecule that is connected to one portion of the reactive hydroxyl-containing molecule, a second acrylate molecule that is connected to a second portion of the a reactive hydroxyl-containing molecule, and a third acrylate molecule that is connected to a third portion of the a reactive hydroxyl-containing molecule to thereby create a multiacrylate hydroxyl-containing molecule or, in other words, a monomeric portion that includes two or more connected to the a reactive hydroxyl-containing molecule.

The formulation of polymer complex compounds with phenols or polyphenols has been the focus of previous work by some of the present inventors. U.S. Pat. No. 8,642,087 sets forth a system for preparing polyphenols by acrylation and subsequent incorporation into a PBAE network to provide a compound with improved bioavailability of the underlying phenol or polyphenol parent compound. In short, preparation of the polyphenol includes the acrylation and subsequent incorporation of polyphenolic compounds into a poly(beta-amino ester) (PBAE) polymer, thereby providing a compound for sustained delivery of such.

Generally, the acrylation step can use a variety of acrylate containing molecules. Non-limiting examples of these acrylate containing molecules may comprises acrylic acid, an ester of acrylic acid, a salt of acrylic acid, a derivative of acrylic acid, methacrylic acid, an ester of methacrylic acid, a salt of methacrylic acid, a derivative of methacrylic acid, or combinations thereof.

The polymer compound comprising a reactive hydroxyl compound may further comprise one or more diacrylate molecules linked to a diamine molecule. Non-limiting examples of diacrylate molecules may be selected from a group consisting of poly(ethylene glycol) diacrylate, diethylene glycol diacrylate, 1,3-butanedioldiacrylate, and combinations thereof.

A wide variety of diamine molecules may be used as a linker such as a primary diamine, a secondary diamine, an aromatic diamine, or combinations thereof. Non-limiting examples of these diamines may be methanediamine, ethylenediamine (EDA), 1,3-diaminopropane, 1,2-diaminopropane, diphenylethylene diamine, isophorone diamine (IPDA), m-xylene diamine (MXDA), p-phenylenediamine, 1,4-diazacycloheptane, 4,7,10-trioxa-1,13-tridecanediamine, or mixtures thereof.

Generally, the molar ratio of acrylate reactive groups to amine reactive groups in the polymer is about 0.25 to about 1.65. In various embodiments, the molar ratio of acrylate reactive groups to amine reactive groups in the polymer is from about 0.25 to about 1.65, from about 0.3 to about 1.5, from about 0.5 to about 1.25, from about 0.75 to about 1.0. In an embodiment, the molar ratio of the acrylate reactive groups to the amine reactive groups is about 1.0. The polymer compound comprises one or more unreactive amines groups.

In general, the delivery composition may be in a number of different forms. Non-limiting examples of these forms may be a hydrogel or a biodegradable film.

The reactive hydroxyl-containing compound comprises a phenolic compound, a polyphenol compound, or a hydroxyl compound. Non-limiting examples of these hydroxyl-containing compounds may be an antioxidant, an antibiotic, an antifungal, an anti-inflammatory, an anti-proliferative, or an antiangiogenic agents.

In one embodiment, the hydroxyl-containing compound may an antioxidant. Non-limiting examples of antioxidants may be 6-hydroxy-2,5,7,8-tetramethylchroman-2-carboxylic acid, tocopherol, (−)-epicatechin, acacetin, apigenin, azaleatin, baicalein, caffeic acid, catechin, chlorogenic acid, chrysin, cichoric acid, a curcuminoid, cyanidin, daidzein, delphinidin, diosmin, ellagic acid, epicatechin, epigallocatechin gallate, eriodictyol, eugenol, eupatorin, galangin, gallic acid, genistein, glycitein, hesperetin, isorhamnetin, kaempferol, luteolin, luteolin, malvidin, matairesinol, myricetin, naringenin, oroxylin A, pelargonidin, peonidin, petunidin, pinoresinol, quercetin, resorcinol, resveratrol, rosmarinic acid, rutin hydrate, silibinin, taxifolin, theaflavin, and analogs thereof.

In another embodiment, the hydroxyl-containing compound may be an antibiotic. Non-limiting examples of suitable antibiotics may be aminoglycosides (e.g., amikacin, gentamicin, kanamycin, neomycin, netilmicin, streptomycin, and tobramycin), carbecephems (e.g., loracarbef), a carbapenem (e.g., certapenem, imipenem, and meropenem), cephalosporins (e.g., cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone), macrolides (e.g., azithromycin, clarithromycin, dirithromycin, erythromycin, and troleandomycin), monobactam, penicillins (e.g., amoxicillin, ampicillin, carbenicillin, cloxacillin, dicloxacillin, nafcillin, oxacillin, penicillin G, penicillin V, piperacillin, and ticarcillin), polypeptides (e.g., bacitracin, colistin, and polymyxin B), quinolones (e.g., ciprofloxacin, enoxacin, gatifloxacin, levofloxacin, lomefloxacin, moxifloxacin, norfloxacin, ofloxacin, and trovafloxacin), sulfonamides (e.g., mafenide, sulfacetamide, sulfamethizole, sulfasalazine, sulfisoxazole, and trimethoprim-sulfamethoxazole), and tetracyclines (e.g., demeclocline, doxycycline, minocycline, and oxytetracycline). In an alternate embodiment, the hydroxyl-containing compound may be an antiviral protease inhibitor (e.g., amprenavir, fosamprenavir, indinavir, lopinavir/ritonavir, ritonavir, saquinavir, and nelfinavir). In still another embodiment, the hydroxyl-containing compound may be a cardiovascular drug. Examples of suitable cardiovascular agents include cardiotonic agents (e.g., digitalis (digoxin), ubidecarenone, and dopamine), vasodilating agents (e.g., nitroglycerin, captopril, dihydralazine, diltiazem, and isosorbide dinitrate), antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril), beta blockers (e.g., levobunolol, pindolol, timolol maleate, bisoprolol, carvedilol, and butoxamine), alpha blockers (e.g., doxazosin, prazosin, phenoxybenzamine, phentolamine, tamsulosin, alfuzosin, and terazosin), calcium channel blockers (e.g., amlodipine, felodipine, nicardipine, nifedipine, nimodipine, nisoldipine, nitrendipine, lacidipine, lercanidipine, verapamil, gallopamil, and diltiazem), and anticlot agents (e.g., dipyrimadole).

In another embodiment, the reactive hydroxyl-containing compound may be an anti-inflammatory agent. Non-limiting examples of anti-inflammatory agents may be a synthetic non-steroidal anti-inflammatory drug (NSAID) such as acetylsalicylic acid, dichlophenac, indomethacin, oxamethacin, ibuprofen, indoprofen, naproxen, ketoprofen, mefamanic acid, metamizole, piroxicam, and celecoxib. In an alternate embodiment, the anti-inflammatory agent may be a prohormone that modulates inflammatory processes. Suitable prohormones having this property include prohormone convertase 1, proopiomelanocortin, prohormone B-type natriuretic peptide, SMR1 prohormone, and the like. In another embodiment, the anti-inflammatory agent may be a corticosteroid to treat inflammation. Examples of corticosteroids include triamcinolone acetonide, betamethasone, dexamethasone, methylprednisolone, and prednisone. In another embodiment, the anti-inflammatory agent may be an enzyme having anti-inflammatory effects. Examples of anti-inflammatory enzymes include bromelain, papain, serrapeptidase, and proteolytic enzymes such as pancreatin (a mixture of trypsin, amylase and lipase).

In still another embodiment, the anti-inflammatory agent may be a peptide with anti-inflammatory effects. For example, the peptide may be an inhibitor of phospholipase A2, such as antiflammin-1, a peptide that corresponds to amino acid residues 246-254 of lipocortin; antiflammin-2, a peptide that corresponds to amino acid residues 39-47 of uteroglobin; S7 peptide, which inhibits the interaction between interleukin 6 and interleukin 6 receptor; RP1, a prenyl protein inhibitor; and similar peptides. Alternatively, the anti-inflammatory peptide may be cortistatin, a cyclic neuropeptide related to somatostatin, or peptides that correspond to an N-terminal fragment of SV-IV protein, a conserved region of E-, L-, and P-selectins, and the like. Other suitable anti-inflammatory preparations include collagen hydrolysates and milk micronutrient concentrates (e.g., MicroLactin® available from Stolle Milk Biologics, Inc., Cincinnati, OH), as well as milk protein hydrolysates, casein hydrolysates, whey protein hydrolysates, and plant protein hydrolysates.

In another embodiment, the reactive hydroxyl compound may be an antifungal compounds. Non-limiting examples of anti-fungal compounds may be clotrimazole, econazole, miconazole, terbinafine, fluconazole, ketoconazole, or amphotericin.

In yet another embodiment, the reactive hydroxyl group may be an antiproliferative agent. Non-limiting examples of non-proliferative agents may be calcineurin inhibitors (cyclosporine and tacrolimus), mTOR inhibitors (sirolimus and everolimus), antiproliferative agents (azathioprine and mycophenolic acid), and corticosteroids.

In still another embodiment, the reactive hydroxyl compounds may be an antiangiogenic agent. Non-limiting examples of antiangiogenic agent may be Axitinib (Inlyta), Bevacizumab (Avastin), Cabozantinib (Cometriq), Everolimus (Afinitor, Zortress), Lenalidomide (Revlimid), Pazopanib (Votrient), Ramucirumab (Cyramza), or Regorafenib (Stivarga).

The delivery composition further comprises a carrier. Suitable carriers can and will vary depending on the polymer used, the acrylate, the diamine, and the reactive hydroxyl group compound employed. Suitable carriers include, but are not limited to, alkane and substituted alkane solvents (including cycloalkanes), aromatic hydrocarbons, esters, ethers, ketones, alcohols, polymeric dispersions, or combinations thereof, and the like. Specific carriers that may be employed, include, for example, polymeric dispersions, acetonitrile, benzene, butyl acetate, t-butyl methylether, t-butyl methylketone, chlorobenzene, chloroform, chloromethane, cyclohexane, dichloromethane, dichloroethane, diethyl ether, ethyl acetate, diethylene glycol, fluorobenzene, heptane, hexane, isobutylmethylketone, isopropyl acetate, methylethylketone, methyltetrahydrofuran, pentyl acetate, n propyl acetate, tetrahydrofuran, toluene, methanol, ethanol, isopropanol, n-propanol, isobutanol, n-butanol, s-butanol, t-butanol, and combinations thereof.

The method further comprises affixing the delivery composition to the substrate. The substrate, in broad terms, may be defined as a material wherein the delivery composition is initially applied and adheres to at least a portion of at least one surface of the substrate. Various methods for affixing the delivery composition are known in the art.

Generally, the substrate may be most any substrate where the hydroxyl reactive compound, once exposed to a trigger, would release the reactive hydroxyl compound. Non-limiting substrates may be a human or non-human animal (such as skin, body part, or organs, or alike), metal, plastic, wood, fabric, cloth, agriculture products (such as grains, fruits, berries, plants), food products, etc.

b. exposing the delivery composition with a trigger.

The method further comprises exposing the delivery composition to a trigger. The trigger, as defined herein, refers to an agent which reacts with the polymer to release the reactive hydroxyl-containing compound from the delivery composition. Non-limiting examples of triggers comprises a reactive oxygen species, a reactive nitrogen species, an oxygen radical, a nitrogen radical, an acid, UV light, an enzymatic species, a macrophage, a leukocyte, a reactive nanoparticle, a metal species, an environmental pollutants, smoke, pesticides, heat, an electrical source, or combinations thereof.

As appreciated by the skilled artisan, the trigger needs to diffuse through the delivery composition, react with the polymer compound to release the reactive hydroxyl compound.

Generally, the rate of release of the reactive hydroxyl compound depends on the amount of the trigger and the strength of the trigger. As appreciated by the skilled artisan, if little or no trigger is presence, the rate of release will be slow. In the presence of a trigger, the rate of release will be accelerated.

II. Systems for Delivering a Reactive Hydroxyl Compound.

Another aspect of the present disclosure encompasses systems for delivering a reactive hydroxyl-containing compound. In general, the system comprises: a. a delivery composition comprising a polymer compound comprising a plurality of monomeric portions each comprising the reactive hydroxyl-containing compound linked to at least two acrylate containing molecules and a plurality of amine linkers, wherein at least one acrylate containing molecule of each monomeric portion is linked by an amine linker to an acrylate containing molecule of an adjacent monomeric portion to thereby forming a polymer; and b. a trigger.

a. delivery compositions

Suitable delivery compositions are described in more detail in Section (I)(a).

b. triggers

Suitable triggers are described in more detail in Section (I)(b).

c. products

The system comprising the delivery composition and the trigger may be incorporated into a number of products.

In one embodiment, the delivery composition and the trigger may be incorporated into cosmetic or personal care products. Non-limiting examples of these products may be sun lotion, shampoo, body wash, cosmetics, soap, tooth paste, oral rinses, lip stick, lip balm, deodorants, cologne, lotions, or perfume.

In another embodiment, the delivery composition and the trigger may be incorporated in pet care and aquarium products. Non-limiting example of these products may be pet or aquarium food, a lotion, a pet treat, or a pet shampoo.

In yet another embodiment, the delivery composition and the trigger may be formulated for application to education products, decorative craft products, or children's toys.

In still another embodiment, the delivery composition and the trigger may be formulated for immediate or times release in agricultural products, agritech products, or lawncare products. Non-limiting examples of the products may be feed, fertilizers, pesticides, or fungicides.

In another embodiment, the delivery composition and the trigger may be formulated into paints and coatings.

In still another embodiment, the delivery composition and the trigger may be formulated for the release of color/flavor compounds for food industry applications.

In yet another embodiment, the delivery composition and the trigger are applied as coatings to implants, restoratives, wound care bandages, gauzes, and other medical device systems.

III. Kits

Another aspect of the present disclosure encompasses a kit for delivering a reactive hydroxyl-containing compound. In general, the kit comprises a delivery composition comprising an amount of polymer compound comprising a plurality of monomeric portions each comprising the reactive hydroxyl-containing compound linked to at least two acrylate containing molecules and a plurality of amine linkers, wherein at least one acrylate containing molecule of each monomeric portion is linked by an amine linker to an acrylate containing molecule of an adjacent monomeric portion to thereby forming a polymer and a trigger. The polymer compound and the amount of the trigger are in separate containers. The kit further comprises instructions for exposing the delivery composition to the trigger.

a. delivery compositions

Suitable delivery compositions are described in more detail in Section (I)(a).

b. triggers

Suitable triggers are described in more detail in Section (I)(b). As appreciated by the skilled artisan, combining the delivery composition and the trigger would allow for accelerated and active release of reactive polyphenolic compound.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "about" when referring to a value or to an amount of mass, weight, time, volume, concentration or percentage is meant to encompass variations in some embodiments of ±20%, in some embodiments of ±10%, in some embodiments of ±5%, in some embodiments of ±1%, in some embodiments of ±0.5%, and in some embodiments of ±0.1% from the specified amount, as such variations are appropriate to perform the disclosed method. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed.

The term "acyl," as used herein alone or as part of another group, denotes the moiety formed by removal of the hydroxyl group from the group COOH of an organic carboxylic acid, e.g., RC(O)—, wherein R is R1, R1O—, R1R2N—, or R1S—, R1 is hydrocarbyl, heterosubstituted hydrocarbyl, or heterocyclo, and R2 is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes saturated hydrocarbyl groups that contain from 1 to 30 carbon atoms. They may be linear, branched, or cyclic, may be substituted as defined below, and include methyl, ethyl, propyl, isopropyl, butyl, hexyl, heptyl, octyl, nonyl, and the like.

The term "alkenyl" as used herein describes hydrocarbyl groups which contain at least one carbon-carbon double bond and contain from 1 to 30 carbon atoms. They may be linear, branched, or cyclic, may be substituted as defined below, and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes hydrocarbyl groups which contain at least one carbon-carbon triple bond and contain from 1 to 30 carbon atoms. They may be linear or branched, may be substituted as defined below, and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The term "aryl" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. They may be straight, branched, or cyclic. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

Having described the invention in detail, it will be apparent that modifications and variations are possible without departing from the scope of the invention defined in the appended claims.

EXAMPLES

The following non-limiting examples illustrate various embodiments of the invention.

Example 1

Materials

Curcumin was purchased from Chem-Impex International, Inc. (Wood Dale, IL). 4,7,10-Trioxatridecane-1,13-diamine (TTD), Tween 80, and 2,2'-azobis(2-amidinopropane) dihydrochloride (AAPH), triethylamine, and acryloyl chloride were purchased from Sigma Aldrich (St. Louis). Poly(ethylene glycol) diacrylate, MW 400 PEG(400)DA), was obtained from Polysciences Inc. (Philadelphia, PA). Dichloromethane (DCM), tetrahydrofuran (THF), dimethylsulfoxide (DMSO) and acetonitrile (ACN) were purchased from Pharmco-Aaper (Brookfield, CT). No additional purification steps were conducted after materials were received.

Preparation of Curcumin Conjugated Poly(beta-amino ester) (PBAE) Microparticle Synthesis Curcumin multiacrylate (CMA) was prepared using an acid chloride-alcohol esterification reaction. Briefly, curcumin and acryloyl chloride were reacted in a 1:3 molar ratio in anhydrous THF in the presence of triethylamine for 24 hours in the dark to comprise a CMA system of 45% curcumin diacrylate, 55% curcumin triacrylate, and 0.9% curcumin monoacrylate characterized by HPLC.

PBAE films were synthesized as follows: CMA and PEG(400)DA were reacted with a diamine crosslinker, TTD, at a ratio of total acrylates to amine protons of 1.0 (RTAAP=1.0) with two different compositions (26 wt % curcumin and 32 wt % curcumin loading). Upon Michael addition, crosslinked PBAE bonds were formed. 1.5 times the total monomer mass of the film of anhydrous DCM was used as the reaction medium. Curcumin was dissolved in half of the anhydrous DCM. PEG(400)DA was added to a separate centrifuge tube with the remaining amount of DCM. TTD was added to the PEG(400)DA/DCM solution and vortexed immediately. After 5 minutes of reaction time at room temperature, the PEG(400)DA/TTD solution was vortexed while CMA was added dropwise quickly and the pre-polymer solution was immediately poured into casting ring on an aluminum covered glass plate and left at room temperature for 1 hour. The film was then transferred to a 50° C. convection oven for 24 hours to complete the reaction and evaporate excess solvent.

Crosslinked films of 0.4 mm thickness were washed for 1 hour at 40 mL per 1 gram of polymer with anhydrous ACN (5 times) to remove any unreacted monomers. Films were placed under vacuum at 50° C. overnight to complete drying. Microparticles were obtained by cutting the film into small pieces and placed into a milling tube with 1 wt % magnesium stearate as a lubricant. Using a 6775 Freezer/Mill Cryogenic Grinder, the film was milled for 10 minutes at 15 cycles per second (CPS), with a pre-cool and post cool setting of 3 minutes. Microparticles were left on the bench top until the tube reached room temperature to prevent any moisture from condensing in to tube. Microparticles were then collected and dried overnight on a lyophilizer to remove any excess moisture and stored at −20° C. in a sealed bag with desiccator pack until future use.

Free Curcumin Stability and Consumption in the Presence of 2,2'-Azobis(2-amidinopropane)Dihydrochloride Curcumin was dissolved at 80 mg/mL in anhydrous DMSO and 6.25 μL was added under constant vortexing to a 10 mL 0.1% (w/v) Tween 80 phosphate buffered saline (PBS) (pH 7.4) solution to reach a final concentration of 50 μg/mL curcumin. Periodic samples were collected and read at 420 nm using a Cary 50 UV-Vis Microplate Reader spectroscopy instrument to monitor absorbance of solution over 24 hours. Curcumin of the same concentration was also introduced to a 10 mM AAPH and 100 mM AAPH 0.1% (w/v) Tween 80 PBS solution and periodic samples were collected and read directly at 420 nm.

Microparticle Degradation Profiles in the Presence of 2,2'-Azobis(2-amidinopropane)Dihydrochloride Microparticle systems were degraded in a 0.1% (w/v) Tween 80 PBS (pH 7.4) solution, 10 mM AAPH/0.1% (w/v) Tween 80 PBS (pH 7.4) or a 100 mM AAPH/0.1% (w/v) Tween 80 PBS (pH 7.4) solution over 24 hours at the same theoretical final release concentration of curcumin. 1 mL samples of the supernatant of the control were collected every two hours and analyzed under UV-Visible Spectroscopy. The volume was replenished after each time point. Independent samples for each time point were prepared for the microparticle release in AAPH solution to maintain a consistent ratio of free radicals to curcumin throughout the 24 hour study.

Microparticle Degradation Product Consumption in the Presence of 2,2'-Azobis(2-amidinopropane)Dihydrochloride Microparticles were fully degraded in a 0.1% (w/v) Tween 80 PBS solution at pH 7.4. AAPH was added to the degradation products to a concentration of either 10 or 100 mM and analyzed directly over time using reverse-phase HPLC (Water Phenomenex C18 column, 5 μm, 250 mm (length)×4.6 mm (ID) on a Shimadzu Prominence LC-20 AB HPLC system) coupled with a UV-Vis detector at 420 nm to analyze curcumin and residual acrylated curcumin peaks over time in the presence of AAPH. The method used was a 20 minute water/acetonitrile gradient supplemented with 0.1% (v/v) phosphoric acid at 1 mL/min that started at 60% water/40% acetonitrile to 0% water/98% acetonitrile over 12 minutes, stayed isocratic for 3 minutes, and then equilibrated back to 60% water/40% acetonitrile for the remaining 5 minutes.

Model Development, Oxidative Consumption Rate of Curcumin

Based on the experimental data collected regarding the consumption profiles of curcumin as a free molecule, a kinetic rate model was developed to describe the oxidative consumption of curcumin. Observing the interactions between three main components in solution (AAPH, free radicals produced, and curcumin) using a first principles approach, a set of rate equations were established. It was assumed that curcumin consumption was solely dependent on the interaction with the radical formed by thermal decomposition of AAPH.

In an AAPH solution, the compound can thermally decompose into either alkyl radical or peroxyl radicals in the presence of molecular oxygen:

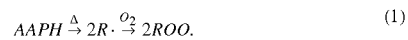

$$AAPH \xrightarrow{\Delta} 2R \cdot \xrightarrow{O_2} 2ROO. \tag{1}$$

It is assumed that radicals are generated upon thermal decomposition of AAPH. As such, a first order rate was assumed ($k_A = 1.26 \times 10^{-6}$ min$^{-1}$) based on Werber et al [22], and can be expressed in the following equation:

$$\frac{dC_A}{dt} = -k_A C_A \tag{2}$$

where $C_A$ is the concentration of AAPH. The thermal decomposition of AAPH produces 2 molecules of radicals for every 1 molecule of AAPH. Based on the instability of general alkyl/peroxyl radicals, the fast half-life and elimination of the free radicals produced are on the order of 1 millisecond [23], which is assumed to be first order (kel=4.16×10$^4$ min$^{-1}$). In an AAPH solution, the concentration of free radicals present can be simplified as:

$$\frac{dC_R}{dt} = 2k_A C_R - k_{el} C_R \tag{3}$$

where $C_R$ is the concentration of free radicals. The change in curcumin concentration is dependent on both the concentration of curcumin and free radicals present over time:

$$\frac{dC_C}{dt} = -k_C C_C C_R \tag{4}$$

where $C_C$ is the concentration of curcumin in solution. In the presence of curcumin, equation (3) can be modified to incorporate the dependence of free radical concentration on the interaction with curcumin present.

$$\frac{dC_R}{dt} = 2k_A C_R - k_{el} C_R - k_C C_C C_R \quad (3a)$$

Oxidative Consumption Rate of Curcumin and Curcumin Monoacrylate Released from the Microparticle Network To better model the consumption rate parameters of the released curcumin ($k_C$) and curcumin monoacrylate ($k_{CM}$) from microparticles, an additional equation, dependent on the free radical concentration, was added to describe the change in concentration of curcumin monoacrylate in the system over time:

$$\frac{dC_{CM}}{dt} = -k_{CM} C_R C_{CM} \quad (5)$$

The free radical concentration is then also dependent on the concentration of curcumin monoacrylate modifying Equation (3a) to the following:

$$\frac{dC_R}{dt} = 2k_A C_R - k_{el} C_R - k_C C_C C_R - k_{CM} C_{CM} C_R \quad (3b)$$

The set of mathematical expressions for the free molecule and degradation products were solved simultaneously using ODE15s in MATLAB while the unknown consumption rate parameters were minimized over the experimental data by sum of squared errors (fminsearch). These parameters were then used to find consumption rate parameters of curcumin monoacrylate found within the solution from the fully degraded microparticle system and the correlation factor was calculated to evaluate the degree of fit.

Demonstration of Controlled Release Antioxidant Delivery

Figure 7:
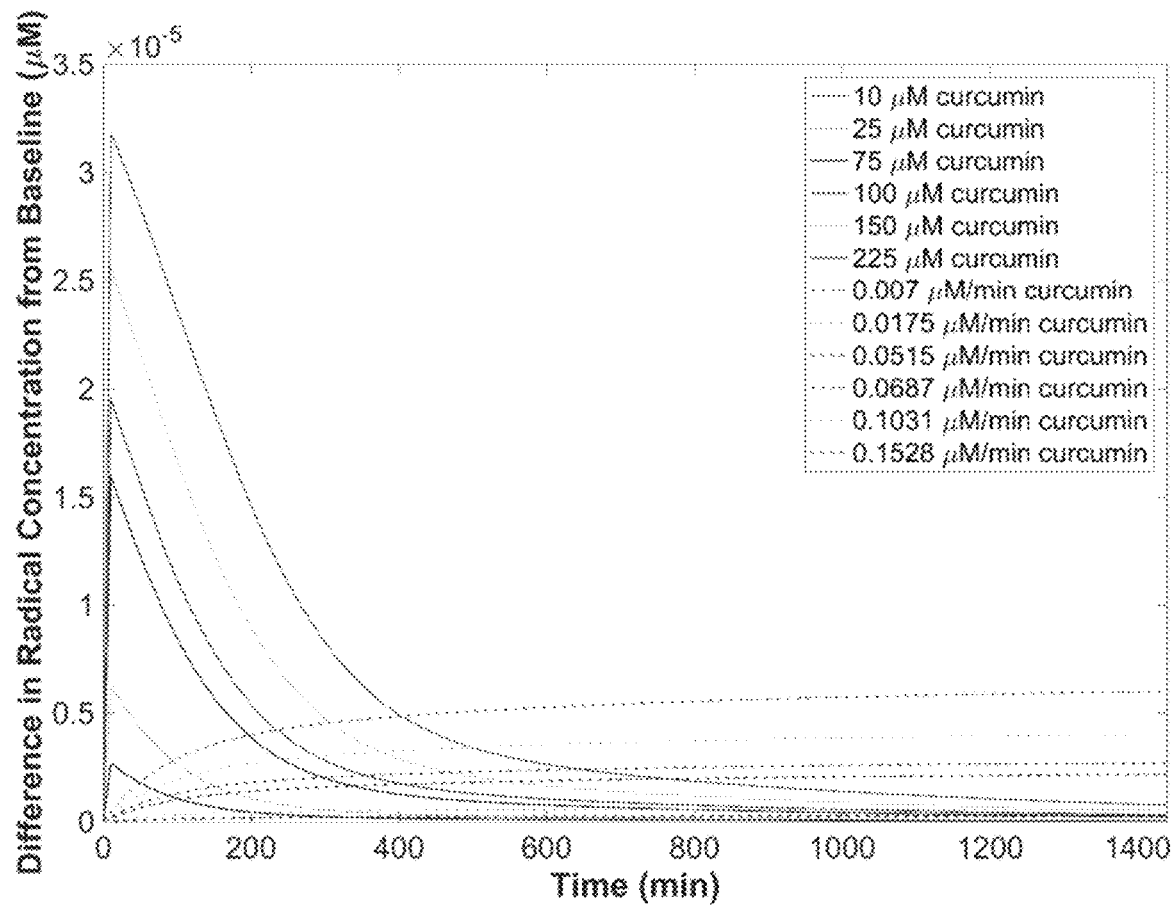
FIG. 7A shows the deviation of free radical concentration ($\mu M$) when the addition of a one-time theoretical injection of free curcumin is added to a 10 mM AAPH solution or the rate equivalent to the total amount added over 24 hours.
FIG. 7B shows the AUC values ($\mu M^*min$) reported as a bar graph.
Figure 7:
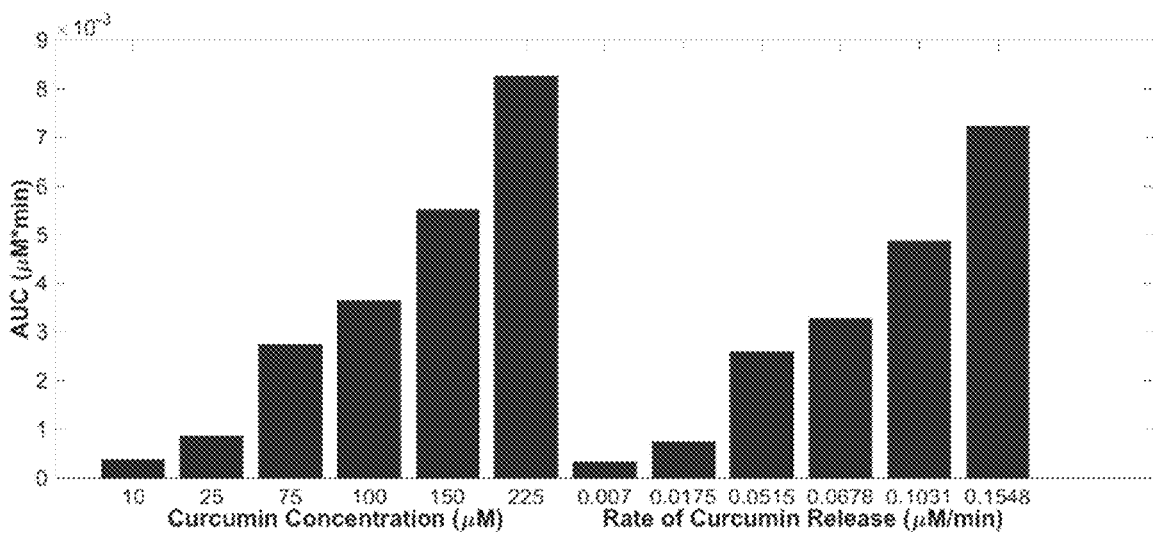

Six zero order rates of curcumin release were investigated and compared to a one-time bolus of the equivalent amount of curcumin over 1440 minutes (FIG. 7). The specified rate was added to the curcumin concentration equation (4) as follows:

$$\frac{dC_C}{dt} = \text{specified rate} - k_C C_C C_R \quad (4a)$$

For one-time delivery treatments, AAPH initial concentration was kept at 10 mM and the only information modified in the model was the initial concentration of curcumin present.

Results and Discussion

Curcumin Conjugated Poly(beta-amino ester) Microparticle Characterization:

Curcumin, characterized by HPLC (FIG. 1A) was successfully modified to a multiacrylate monomer (FIG. 1B) to be incorporated into the PBAE network. The shift in retention time is due to the addition of acrylate groups to the molecule. The peaks were compared to Patil et. al. to identify the monoacrylate, diacrylate, and triacrylate retention times and percentages[21]. Poly(curcumin) films (FIG. 1C) were successfully synthesized and cryomilled (FIG. 1D). Size distribution of the microparticles were characterized using a Size Analyzer (Shimadzu SALD-7101) and ranged from 25-100 μm (FIG. 1E). Degradation studies of the two systems individually and blended at a 50:50 ratio was conducted in a 0.1% (w/v) Tween 80 PBS (pH 7.4) solution to quantify the cumulative release of curcumin over time. Curcumin release was monitored using an ultra-violet visible spectroscopy at curcumin's maximum absorbance wavelength of 420 nm. Upon introduction of PBAE microparticles to a 0.1% (w/v) Tween 80 PBS solution, base-catalyzed hydrolysis occurs and the ester bond is cleaved by a nucleophilic attack from a water group present; however, the rate of hydrolysis is dependent on the degree of hydrophobicity of the polymer backbone. As hydrophobicity increases, the rate of release decreases, slowing the curcumin release rate. The 26 wt % loaded curcumin microparticles, with a higher incorporation of the hydrophilic co-monomer, PEG(400)DA, released curcumin over 8 hours until the absorbance values plateaued. When incorporating a higher amount of CMA in to the backbone of the network, the rate of release is extended over a 12 hour period. For each bulk film system, there is a point at which the integrity of the film is lost and a burst release can be observed. Due to the increase in surface area of the microparticle system, the burst release phenomenon is minimized and the release profile appears more linear compared to bulk film degradation. To form a constant release, the 26 wt % and 32 wt % loaded curcumin microparticles were blended at a 50:50 ratio. By incorporating the 26 wt % microparticle system and the 32 wt % microparticle system, the faster release took place initially and the slower rate of release dominated after 6 hours, taking on a constant rate of release with an $R^2=0.98$ when comparing to a constant slope trendline (FIG. 1F).

Consumption Profiles of Curcumin

Figure 2:
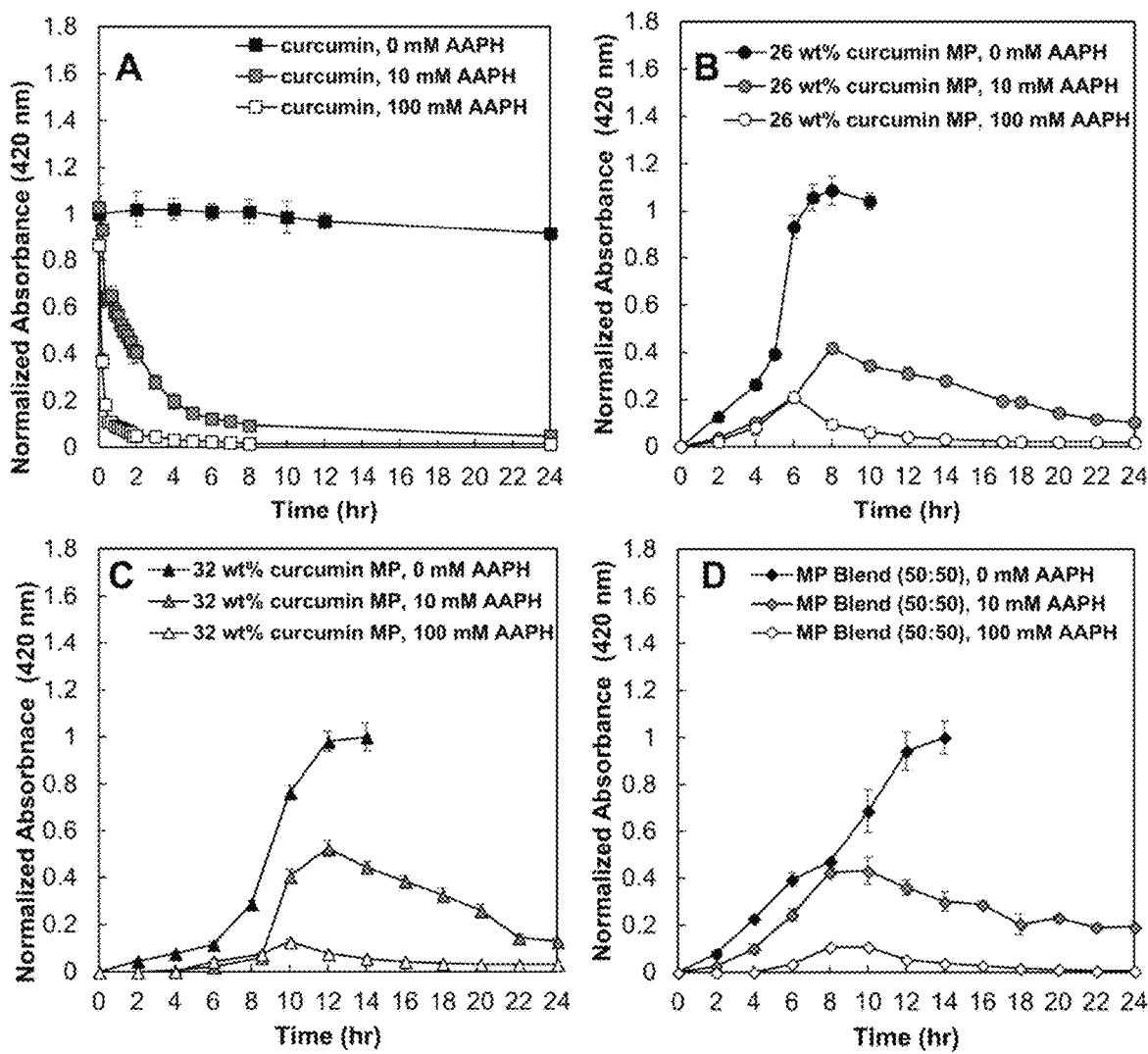
FIG. 2A shows profiles of curcumin over time.
FIG. 2B shows 26 wt % curcumin loaded PBAE MP.
FIG. 2C shows 32 wt % curcumin loaded PBAE MP.
FIG. 2D shows a 50:50 blend of 26 and 32 wt % loaded MPs in the presence of 0, 10 and 100 mM AAPH over 24 hours (M±SEM, n=3).

The absorbance of a 50 μg/mL curcumin solution in 0.1% (w/v) Tween 80 PBS (pH 7.4) was monitored to evaluate curcumin stability at 37° C. (FIG. 2A). As shown, there was no significant change in absorbance, as well as no precipitation in solution, suggesting that curcumin was stable for over 24 hours in aqueous solution. However, when in the presence of AAPH, curcumin's absorbance profile dramatically changes over time. As free radicals are generated in solution, curcumin protons are abstracted leading to destabilization of the molecule and degradation of curcumin. As curcumin degrades, it loses its characteristic absorbance at 420 nm (FIG. 2B). The rate of curcumin consumption is correlated to the initial concentration of AAPH in solution. 10 mM AAPH solution results in 90% of curcumin consumed within the first 8 hours, whereas 100 mM AAPH solution results in 90% of curcumin consumed within the first hour.

Figure 3:
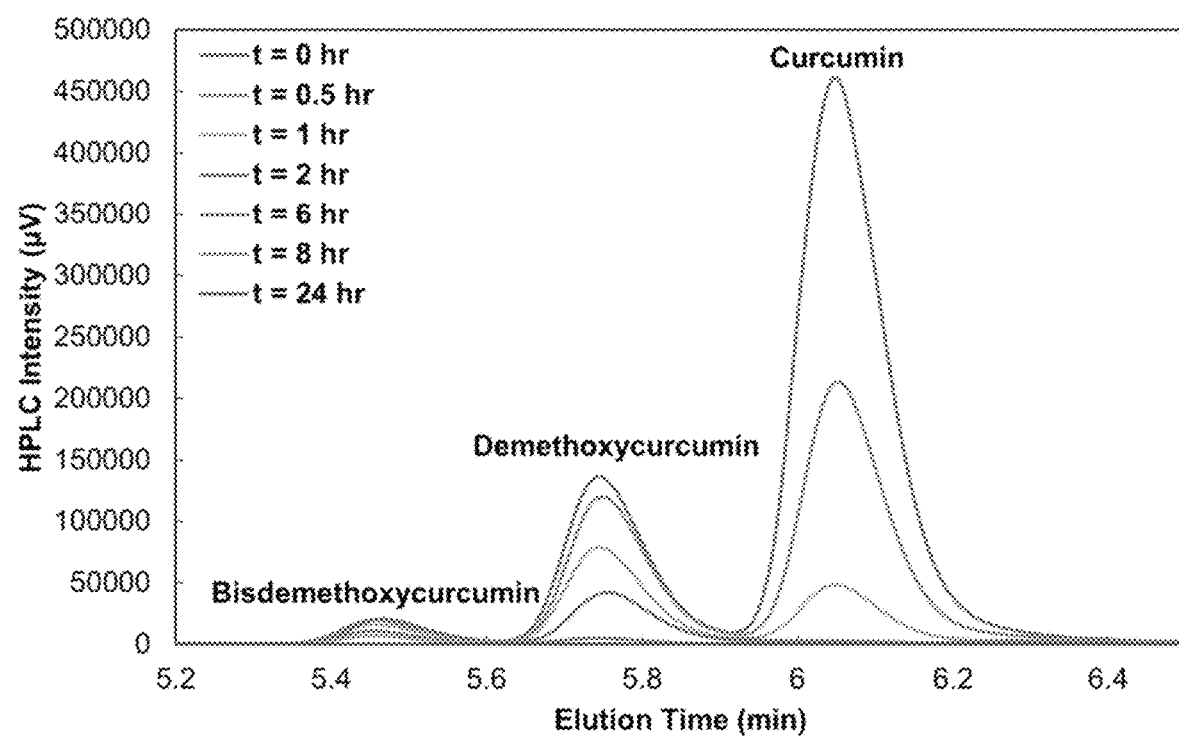
FIG. 3 shows curcuminoid consumption susceptibility by AAPH over time.

Using HPLC, the consumption of the curcuminoids was investigated. The three forms of curcumin (curcumin, curcumin demethoxycurcumin, and bisdemethoxycurcumin) found in solution were consumed in order of antioxidant activity [24], being that the curcumin peak diminished at a faster rate than demethoxycurcumin, and bisdemethoxycurcumin (FIG. 3). Overall, curcumin appears to be highly susceptible to depletion in AAPH solutions at all times as its hydroxyl sites on each curcuminoid are always exposed.

Microparticle Degradation Profiles in the Presence of 2,2'-Azobis(2-amidinopropane)Dihydrochloride 26 wt % curcumin loaded PBAE MPs were introduced to both 10 and 100 mM AAPH 0.1% (w/v) Tween 80 PBS solutions at pH 7.4 in a 37° C. agitating shaker bath (FIG. 2B). The profile of the microparticle release in the presence of AAPH changed significantly compared to the release profile with 0 mM AAPH. Incorporating curcumin in to the backbone of PBAE crosslinked network provided protection from oxidation until released from the network. As the network hydrolytically degrades and releases intact curcumin, its exposed protons are able to be abstracted from the free radicals present. As curcumin is released, it is also consumed at a rate in which it is interacting with the free radical. Once the curcumin is released in its entirety and the microparticles are fully degraded after eight hours, the residual curcumin released in to solution begins to be consumed; however, the rate of consumption appears to be slower compared to free curcumin and after 24 hours there is still is curcumin present based on absorbance. The controlled release of curcumin allowed for sustained concentrations of curcumin over an extended period compared to the exponential consumption seen of curcumin as a free drug. 32 wt % curcumin loaded PBAE MP was also introduced to AAPH (FIG. 2C). Initially less curcumin is recovered in the system, due to its slower release rate. The profile shifts its max amount of curcumin in solution with AAPH, where 40% of the absorbance is retained from the first eight hours in the 26 wt % MP to 12 hours in the 32 wt % MP system. Again, after all of the curcumin has been released, the absorbance starts to decrease as the free curcumin in solution is consumed, but likewise to the other system, 10% of the absorbance remains even after 24 hours. Similar trends are seen at high concentrations of AAPH for both 26 and 32 wt % MP networks; however the peak absorbance recovery is shifted by 2 hours, the overall recovery is lower, and all of the colorimetric products are consumed by 24 hours. For 100 mM AAPH, no color absorbance is seen after 12 hours and 20 hours respectively. To try and extend the curcumin in solution for a constituent amount of time, the 50:50 MP blend was evaluated as well (FIG. 2D). Within the first 8 hours, 42% of recovery is obtained from the microparticle system, and due to the extended release contribution from the 32 wt % microparticles in solution, the recovery at 40% was held constant between 8 and 10 hours, before a decrease in recovery was seen. Similarly, the blend in the presence of the 100 mM AAPH was consumed at a faster rate, but also had a constant recovery of 15% for 2 hours before it began to be consumed over the remaining 18 hours. When observing free curcumin in the presence of 10 mM AAPH and 100 mM AAPH, the amount of curcumin decreases to 20% after 4 hours and 20 minutes respectively. For the controlled release mechanisms, the curcumin has sustained recovery above 20% for up to 16 hours out of the 24 hour duration. For the 100 mM AAPH solution, the recovery of curcumin is highest in 26 wt % as the rate of release of curcumin dominates the generation of radicals that would consume the active component over time. The slower release provides a slow enough rate to allow for a consistent consumption of curcumin over time, where curcumin recovery levels are low throughout the entire duration of release.

Due to the residual absorbance retained at 24 hours in all release curves interacting with 10 mM AAPH (FIGS. 2B-2D) and the change in extent of consumption after the microparticles have been fully degraded, HPLC analysis was used to verify the degradation products present after the microparticle system had been completely degraded. After running the supernatant of a fully degraded microparticle system via HPLC, all three forms of curcumin (curcumin, demethoxycurcumin, and bisdemethoxycurcumin) peaks were observed in FIG. 4A at an elution time of 5-6.5 minutes; however, residual curcumin monoacrylate peaks at elution times between 8-9 minutes were observed as well, verified by a curcumin multiacrylate standard. The residual acrylates found in the supernatant could be a result of a curcumin triacrylate group being unable to fully crosslinked at all three sites due to steric hindrance of the curcumin molecule during film synthesis. This would allow for hydrolysis to retain 2 phenol groups, but leave a residual unreacted acrylate group on the molecule. The additional acrylate moiety found on the molecule appeared to influence susceptibility of consumption, explaining the residual color left in solution over 24 hours and the change in overall rate of consumption.

Figure 4:
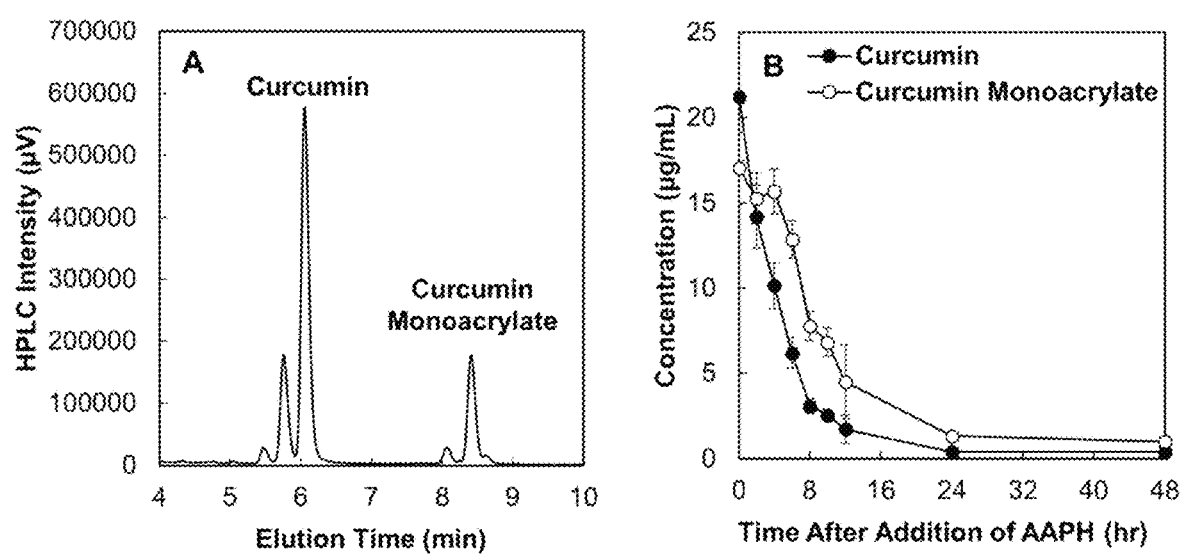
FIG. 4A shows HPLC chromatogram of the curcumin and curcumin monoacrylate peaks found in the supernatant of a fully degraded microparticle system.
FIG. 4B shows the independent consumption profiles of curcumin and curcumin monoacrylate in the presence of 10 mM AAPH (M±SEM, n=3).

26 wt % microparticles were fully degraded in a 0.1% (w/v) Tween 80 PBS solution at pH 7.4. 10 mM AAPH was introduced to the solution with the released products, and the consumption profiles of curcumin and curcumin monoacrylate were monitored using HPLC (FIG. 4B). Curcumin was consumed over time at a consistent rate as seen before as a free molecule (FIG. 2A); however, curcumin monoacrylate peaks in the chromatogram do not begin to decrease until 4 hours after the addition of 10 mM AAPH and then begin to be consumed. This lag could be due to decrease in antioxidant activity with the presence of the acrylate group on close to 40% of the curcumin molecules that are released; however, it was able to possess activity and was still consumed over time. There is also residual concentration of curcumin monoacrylate at 24 hours.

Development of the Oxidative Consumption Rate Model of Free Curcumin

Figure 5:
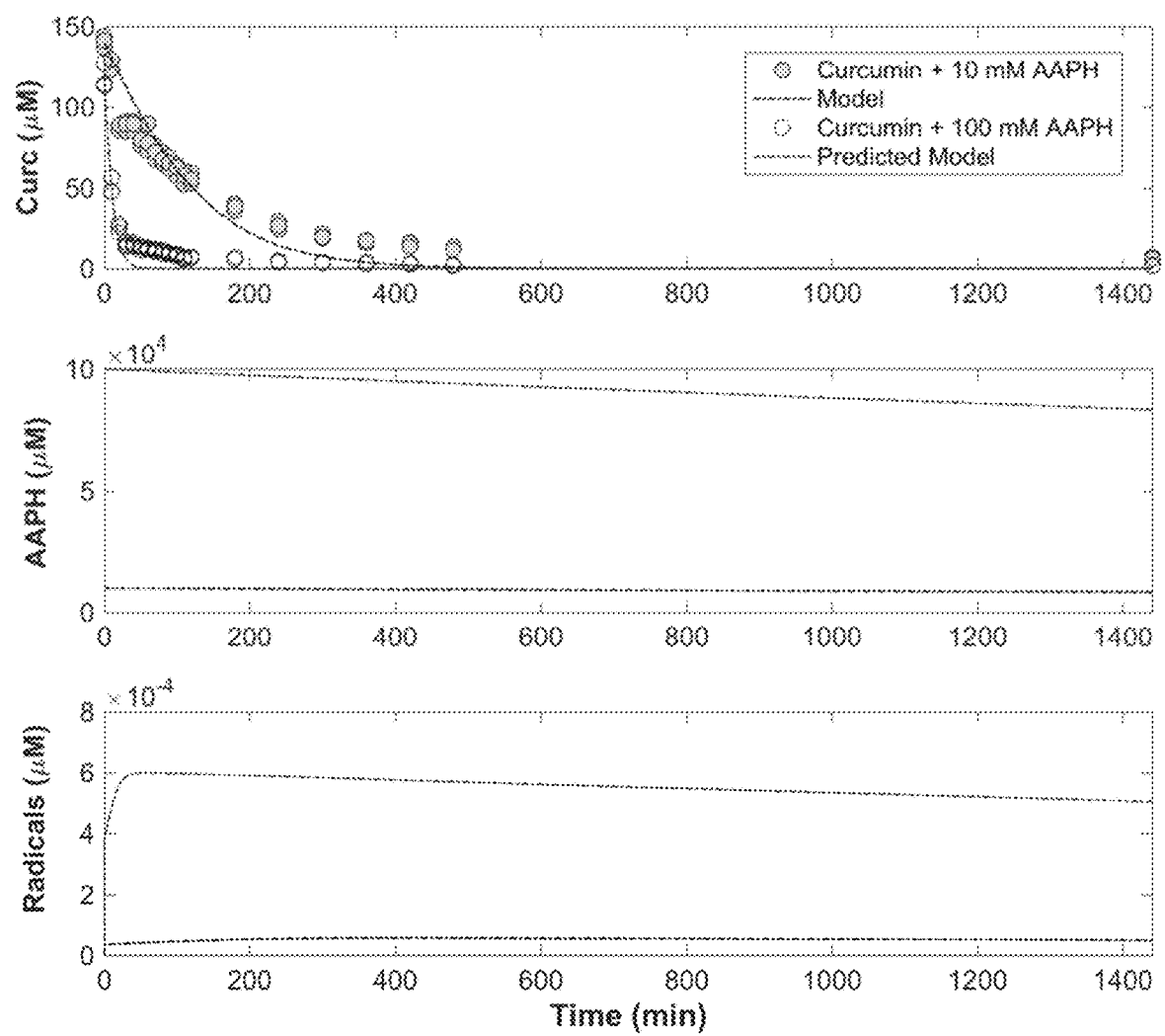
FIG. 5 shows model for curcumin consumption (dashed line) minimized based on raw experimental data of degradation products in the presence of 10 mM AAPH and verified by overlaying model with raw experimental data with higher initial AAPH concentration.

Using the experimental data obtained from curcumin in the presence of 10 mM AAPH (FIG. 2A), equations (2), (3a), and (4) were solved simultaneously using MATLAB ODE15s solver and the fminsearch function to find the unknown consumption parameter, $k_C$, to be 200 $\mu M^{-1} min^{-1}$ with $R^2$=0.895 in comparison to the experimental data (FIG. 5). Equation (4) is plotted in the first subplot, where Equation (2) and (3a) are plotted in the second and third subplot. The model was verified by plotting the expected profile of curcumin consumption in a 100 mM AAPH solution and was compared to the experimental data of curcumin consumption in 100 mM AAPH over time. The consumption profile of curcumin exponentially decreased, and the entirety of curcumin was theoretically consumed within the first hour. Although the finality of curcumin consumption was not until 8 hours experimentally, the majority of curcumin was consumed within the first hour, just as the model described. The consistency in predicted curcumin consumption profile verified second order degradation kinetics to describe the consumption of curcumin in the presence of AAPH. Correlation factor values are provided in Table 1. AAPH concentration decreased over time as the thermal decomposition of the molecule of takes places. The concentration of free radicals started to increase as the free radicals were generated and then began to decrease as the elimination constant within the equation dominated after all the curcumin was consumed. This model was able to predict the consumption profile of curcumin over time in a solution of higher radical concentration at a correlation factor of 0.92.

TABLE 1

Oxidative consumption rates and correlation factors for the minimized and predicted curcumin consumption profile.

| Model | $k_c$ ($\mu M^{-1} min^{-1}$) | $R^2$ |
|---|---|---|
| Curcumin + 10 mM AAPH | 200 | 0.895 |
| Curcumin + 100 mM AAPH | 200 | 0.915 |

Figure 6:
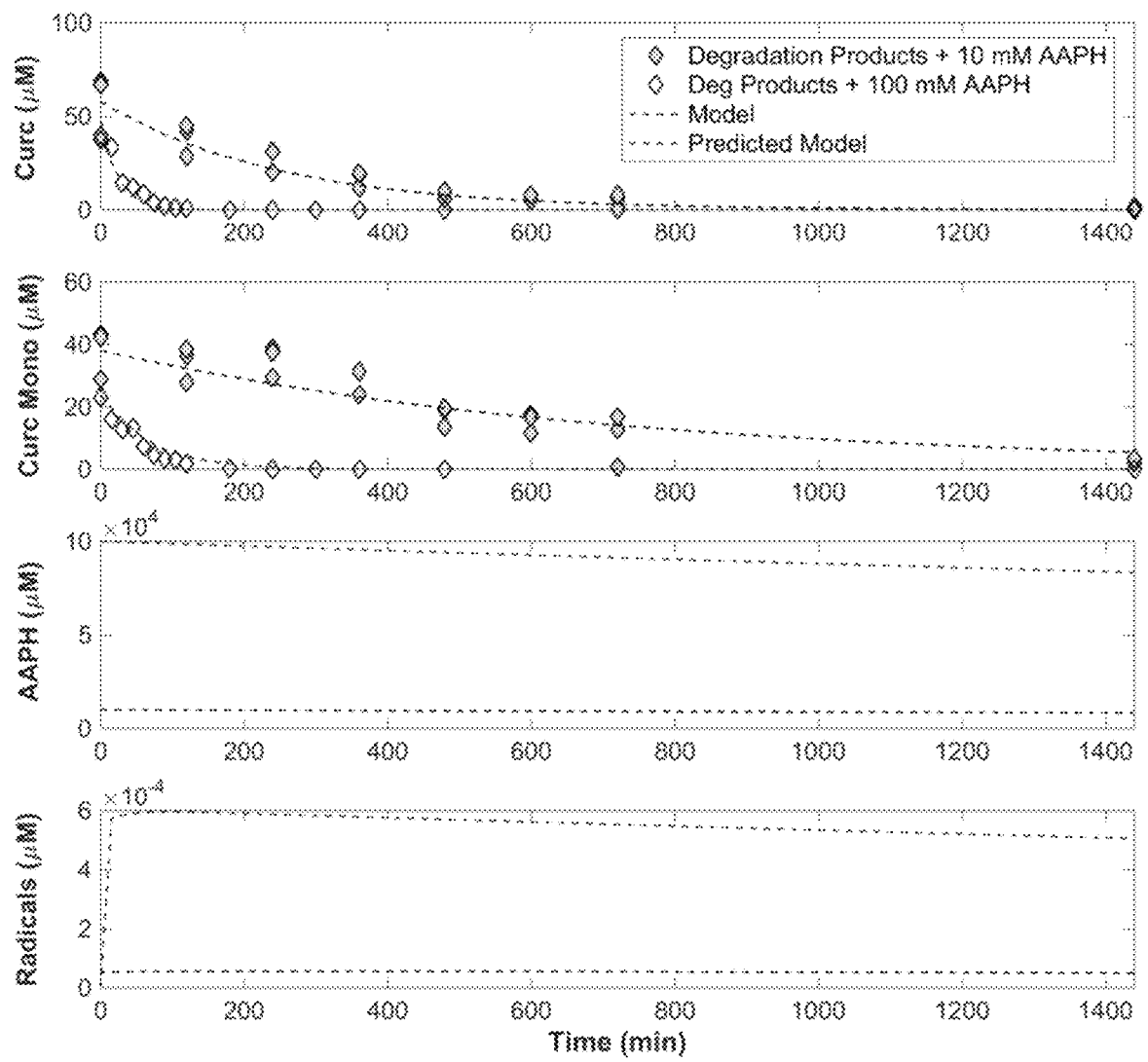
FIG. 6 shows model (dashed line) minimized based on experimental data of degradation products in the presence of 10 mM AAPH (gray diamond) and verified by overlaying predicted model with experimental data with higher initial AAPH concentration (white diamond).

Modeling the Consumption of Released Products in the Presence of 2,2'-Azobis(2-amidinopropane)Dihydrochloride Equation (5) was added to the set of equations to describe the consumption rate of the curcumin monoacrylate released. Equations (2), (3b), (4), and (5) were solved simultaneously as previously described and $k_C$ and $k_{CM}$ were minimized fitting the HPLC experimental results to 75 $\mu M^{-1}min^{-1}$ and 25 $\mu M^{-1}min^{-1}$, respectively (FIG. 6). It is here we note that the oxidative consumption rate of curcumin has decreased in comparison to the oxidative consumption rate of curcumin as a free molecule. This suggests the activity of curcumin was slightly inhibited in the presence of residual degradation products from the polymer network in solution or from being integrated within the network. The model was then used with the minimized parameters to predict consumption profiles of curcumin and curcumin monoacrylate in the presence of 100 mM AAPH and overlaid with experimental data. Indeed, the rate parameter of curcumin monoacrylate was lower; however, when predicting consumption profiles in a higher concentration of free radicals, the model fit well at a correlation factor of 0.924, again providing validity to the second order kinetic rate model for the products released from the network (Table 2).

The free radical levels present over time in this model (FIG. 6, subplot 3) appeared to be more constant than in the curcumin model with a low but instantaneous production of free radicals, thus decreasing slightly over time due to the elimination rate term. Within both the curcumin and release product models (FIGS. 5 and 6), the fit appears to deteriorate slightly over time. This could be due to the $k_C$ and $C_C$ terms describing curcumin as an overall component. The starting material used was a mixture of three curcuminoids with curcumin as the majority of mixture (85%). Proven in FIG. 3, curcumin has the fastest consumption rate compared to demethoxycurcumin and demethoxycurcumin. Because these three compounds were described as one consumption rate, the relative consumption will be skewed to the most active form, and therefore model a faster consumption profile overall.

For the treatment of an oxidative stress induced disease such as oral mucositis, the application of curcumin conjugated PBAE microparticles to the surface of the buccal cheek pouch could allow for controlled release of curcumin to suppress free radical production that activates pro-inflammatory markers. When translating this model into a human or in vivo studies, other pathways of elimination of curcumin may be added. A potential missing term or "piece to the puzzle" would be a rate to describe the wash out of particles, which would account for any loss of curcumin that was removed before release. This would take in to account the retention time of particles on the surface of the buccal tissue. Retention time can be enhanced by using a vehicle such as a mucoadhesive solution, but this term would and should be incorporated in future development of models to predict lasting effects in vivo.

Another factor that could play a role in the discrepancy of the consumption profiles is the rate of hydrolysis versus rate of swelling. While PBAE crosslinked networks are degradable, they are also classified as hydrogels due to their swelling properties. The domination of swelling effects in initial release profiles can be demonstrated, where in each independent microparticle network, there is a point at which microparticle integrity is lost, allowing for the remainder of the curcumin to be released. The consumption equations developed could then be added to describe the products of interest in the presence of AAPH.

The model developed demonstrates the ability to describe curcumin and curcumin monoacrylate in the presence of a free radical, like AAPH, and has promising results to better understand free radical interaction of curcumin in vivo. The consumption rate of curcumin and curcumin monoacrylate in the presence of AAPH was successfully described by this nonlinear model; however, consumption rates of these compounds could change based on the origin and property of the free radical present. It has been shown that the activity of scavenging potential changes based on the interaction of radicals. Curcumin has been presented as having a high reducing power to transition metals, a value correlated to antioxidant capacity, but when investigated with specific free radical interactions, lower scavenging potentials are found for superoxide anions and $H_2O_2$ compared to AAPH. In the future, this model could be investigated and compared against consumption profiles of other free radical molecules to better understand the degree of translation in other environments and the authenticity this model has to AAPH specifically.

TABLE 2

Oxidative consumption rates of curcumin and curcumin monoacrylate release from microparticle networks.

| Model | $k_C$ ($\mu M^{-1}min^{-1}$) | $k_{CM}$ ($\mu M^{-1}min^{-1}$) | $R^2$ |
|---|---|---|---|
| Degradation Products + 10 mM AAPH | 75 | 25 | 0.876 |
| Degradation Products + 100 mM AAPH | 75 | 25 | 0.924 |

Demonstration of Controlled Release Antioxidant Delivery

The deviation of free radical concentrations by adding curcumin at a constant rate or at one initial amount was compared. The theoretical baseline generated at a concentration of 10 mM AAPH was the point of deviation. The plot shown in FIG. 7A represents the concentration deviation from the baseline concentration of free radicals over time in the presence of bolus curcumin doses or constant release rates of equivalent curcumin over 24 hours, where $C(t=0)=0$ $\mu M$. For 10 and 25 $\mu M$ curcumin initial concentrations, the change in free radical concentration was $0.25 \times 10^{-5}$ and $0.6 \times 10^{-5}$ $\mu M$ initially and reverted to baseline within less than 2 hours after all the curcumin had been consumed. Bolus delivery of low concentrations allowed for a fast, initial consumption of radicals present, and deviated significantly from the baseline level of radical concentration. The curcumin was then quickly consumed, and the initial free radical levels were maintained. Higher initial concentrations such as 225 $\mu M$ curcumin deviated significantly at t=0 min by $3.25 \times 10^{-5}$ $\mu M$ and did not reach baseline until after 24 hours. The greater the initial dose of curcumin, the longer it took for the free radical concentration to reach baseline, which initially could appear as a benefit; however, the greater the deviation in antioxidant/oxidant levels, the higher the risk in implementing imbalance to the cellular environment. This could ultimately create an antioxidant toxicity effect by shifting the redox equilibrium in the environment. This model represents the potential risk of toxicity by showing the drastic change in concentration initially.

When utilizing the model with curcumin at a constant rate of release over 24 hours, the deviation of free radical concentration did not appear as significant compared to the bolus dose delivery method. Unlike bolus doses of curcumin, the controlled release of even the highest theoretical delivery of 225 µM over 24 hours only deviated from baseline levels by $0.6 \times 10^{-5}$ µM at any time in the 24 hour period evaluated. To understand the degree of curcumin's scavenging potential and the degree in change of the free radical environment, the area under the curve (AUC) for each delivery method was evaluated (FIG. 7B). For the curcumin rates of release, the AUC ranged from $3.34 \times 10^{-4}$-$7.3 \times 10^{-3}$ µM*min, and for initial doses of curcumin, the AUC ranged from $3.84 \times 10^{-4}$-$8.3 \times 10^{-3}$ µM*min (FIG. 7C). For all bolus deliveries, the AUC was higher than all the controlled release models, showing greater change in antioxidant/oxidant levels in bolus deliveries for each theoretical dose equivalence.

TABLE 3

Summary of the total area under the curve of each theoretical dose

| Initial Dose (µM) | AUC (µM * min) | Rate of Release (µM/min) | AUC (µM * min) |
|---|---|---|---|
| 10 | $3.84 \times 10^{-4}$ | 0.0070 | $3.34 \times 10^{-4}$ |
| 25 | $8.72 \times 10^{-4}$ | 0.0175 | $7.56 \times 10^{-4}$ |
| 75 | $2.7 \times 10^{-3}$ | 0.0515 | $2.6 \times 10^{-3}$ |
| 100 | $3.7 \times 10^{-3}$ | 0.0678 | $3.3 \times 10^{-3}$ |
| 150 | $5.5 \times 10^{-3}$ | 0.1031 | $4.9 \times 10^{-3}$ |
| 225 | $8.3 \times 10^{-3}$ | 0.1548 | $7.2 \times 10^{-3}$ |

Conclusions

In these novel controlled delivery systems, the consumption of curcumin was protected as it was incorporated into the backbone of the microparticle network until hydrolyzed and released into the environment. The experimental findings in this work showcased the ability to deliver a constituent amount of curcumin over time through a controlled release system compared to rapid consumption as a free drug. Experimental data provided a foundation to develop a second order kinetic rate model to describe the oxidative consumption of curcumin as a free molecule and the oxidative consumption of the materials released from the microparticle network utilizing a first principles process. This gives insight on the incorporation of an antioxidant into the backbone of a polymer and how the addition of curcumin into a network allows for more consistent delivery and protection of curcumin over time. It also showed that controlled release can suppress levels of free radicals theoretically over time consistently rather than dramatically, which is not possible with bolus delivery of curcumin. This model will continue to be developed to advance the pharmacokinetics of curcumin conjugated poly(beta-amino ester) networks and implement them into clinical practice in the future.

Example 2

Polyphenol Conjugated Poly(beta-amino ester)Polymers Possess Hydrogen Peroxide Triggered Degradation and Active Antioxidant Release Up until now, the hydrolysis of the poly(beta-amino ester) (PBAE) networks has been thought to be predominantly controlled by base catalyzed hydrolysis, where water acts as the nucleophile to attack at the ester site to promote cleavage. Responsiveness of linear PBAE polymer degradation to external stimuli has been studied by many laboratories to deliver plasmid DNA for gene therapy using DNA/polymer complexes, as well as tuning the degradation of linear PBAE polymers in acidic environments by adding acid sensitive monomers. PBAEs have also been designed to contain bioreducible properties for intracellular delivery of siRNA utilizing unique disulfide PBAE linkages, which degrade specifically from redox potential through thiol-disulfide exchange in the cytosol where high concentrations of glutathione are present. However, the response to oxidative environments, specifically $H_2O_2$, in crosslinked PBAE networks has yet to be studied.

In this work, it is demonstrated for the first time that physiologically relevant concentrations of $H_2O_2$ in solution can trigger accelerated degradation of the curcumin conjugated crosslinked PBAE networks, hydrolyzing curcumin at a self-regulating rate dependent upon the concentration of $H_2O_2$ and curcumin incorporated into the backbone of the network. Curcumin, a small hydrophobic polyphenol with high antioxidant capacity has promise as a therapeutic, but because of curcumin's high reactivity and instability as a free molecule, there is motivation to demonstrate preservation of the active sites until antioxidant treatment is desired in an environment. This peroxide mediated mechanism of degradation can release curcumin in a self-regulated fashion, where the local levels $H_2O_2$ can control the "as needed" delivery of curcumin to counterbalance oxidative environments. In this work, $H_2O_2$ mediated release and polymer degradation is compared to another oxidizing environment, 2'2-azobis(2-amidinopropane) dihydrochloride (AAPH), a thermally decomposing free radical generator, which appears to have negligible effect on the cleavage of the network, but promotes consumption of curcumin once released into the environment. Peroxide mediated release takes advantage of the oxidizing environment to appropriately regulate the delivery of curcumin necessary for potential treatment and balance in an oxidatively rich environment. This will help to deliver a necessary amount of curcumin at sites of high producing $H_2O_2$ concentrations to counteract oxidative stress induced diseases.

Materials 4,7,10-Trioxatridecane-1,13-diamine (TTD), Tween 80, 2,2'-azobis(2-amidinopropane) dihydrochloride (AAPH), 2,2'-azino-bis(3-ethylbenzothizoline-6-sulphonic acid) (ABTS), ammonium persulfate (APS), triethylamine, hydrogen peroxide (H2O2), and acryloyl chloride was obtained from Sigma Aldrich (St. Louis). Curcumin was purchased from Chem-Impex International, Inc. (Wood Dale, IL). Poly(ethylene glycol) (MW 400) diacrylate (PEG(400)DA), was obtained from Polysciences, Inc (Philadelphia, PA). Dichloromethane (DCM), tetrahydrofuran (THF), and acetonitrile (ACN) were purchased from Pharmco-Aaper (Brookfield, CT). No additional purification steps were conducted after materials were received.

Synthesis of Bulk PBAE Films

PBAE bulk films of four different weight loading percentages of curcumin were synthesized similar to Patil et al[15]. The compositions are found in Table 4. Briefly, to modify curcumin into a multiacrylate system, curcumin was dissolved in anhydrous THF. In the presence of triethylamine, acryloyl chloride was added at a 1:3 molar ratio under purged nitrogen in an ice bath. The acid-chloride esterification reaction was left for 16 hours to modify the hydroxyl sites of curcumin to acrylate groups, forming a curcumin multiacrylate (CMA) mixture. The CMA product was purified by removing the excess acrylic acid and TEA-HCl salts formed as by products during the reaction, and the product was verified by high performance liquid chromatography (HPLC) and resulted in a mixture of less 0.9% curcumin monoacrylate, 45% curcumin diacrylate, and 55% curcumin triacrylate.

TABLE 4

Compositions of curcumin conjugated poly(beta-amino ester) films all synthesized at a ratio of total acrylate to amine protons (RTAAP) of 1.0.

| CMA (mol %) | PEG(400)DA (mol %) | Curcumin (wt %) |
|---|---|---|
| 0 | 100 | 0 |
| 20 | 80 | 10 |
| 50 | 50 | 26 |
| 60 | 40 | 32 |

Curcumin conjugated PBAE networks were synthesized using Michael addition chemistry, reacting CMA and PEG (400)DA at different ratios with a primary diamine crosslinker, TTD, at a ratio of total acrylate to amine protons (RTAAP) of 1.0 in anhydrous DCM at 1.5 times the total monomer mass of the film. Films were left at room temperature for 1 hour and then transferred to a 50° C. convection oven for 24 hours. Films were then subject to five 1 hour washes in anhydrous acetonitrile at 40 mL per 1 g of film to remove unreacted monomers from the network. After the washes, films were then dried at 50° C. under vacuum and stored with a desiccant until use.

Swelling Profiles in the Presence of AAPH or $H_2O_2$

Circular discs from a bulk film of 0.4 mm thickness were punched and placed in 20 mL of 0.1% (w/v) Tween 80 PBS solution (pH 7.4). Solutions of 0.5, and 5 mM AAPH solutions, or 0.5 and 5 mM $H_2O_2$ were also prepared to be used for the swelling and release studies. Samples (n=3) were submerged in an agitating shaker bath at 37° C. At desired time points, films were removed from the bath, blotted dry on a tissue, and the mass was measured. The swelling ratio is defined as:

$$\text{Swelling Ratio} = \frac{M_S}{M_I} \quad (1)$$

where $M_S$ is the mass of the swollen film and $M_I$ is the mass of the initial disk. The swelling ratio was observed until the film lost mechanical integrity and could no longer be handled.

Total Polymer Content in the Presence of AAPH or $H_2O_2$

Individual films (n=3) for each time point were measured to obtain the percent of polymer mass remaining over time in a 0.1% (w/v) Tween 80 PBS (pH 7.4) and compared to solutions with AAPH or $H_2O_2$. Empty microcentrifuge tubes were weighed. At each time point, films were removed from the bath, blotted dry on a tissue, and the swollen mass was measured. The polymer was then collected in a microcentrifuge tube and frozen at −20° C. Films were then lyophilized overnight, and the mass of the microcentrifuge tube plus the dried mass was measured. Knowing the mass of the swollen polymer ($M_S$) and the initial mass of the polymer ($M_I$), the amount of water retained by the film is known ($M_W$) and calculated using the following equation:

$$M_W = M_S - M_I \quad (2)$$

After the swollen film was freeze-dried, the salts from the buffer remained. The theoretical amount of residual salts was calculated from the mass of the known water and the salts were subtracted from the dried polymer mass to obtain the mass of the dried film. The mass remaining percentage is defined as the following:

$$\% \text{ Mass Remaining} = M_{FR}/M_I \quad (3)$$

where $M_{FR}$ is the mass of the film dried that remained. Films were compared by evaluating the time at which 50% of the total polymer mass remains and reported as MT50.

Release Profiles in the Presence of AAPH or $H_2O_2$

The release of curcumin and curcumin monoacrylate from the film were measured via reverse-phase high performance liquid chromatography (HPLC) (Water Phenomenex C18 column, 5 μm, 250 mm (length)×4.6 mm (ID) on a Shimadzu Prominence LC-20 AB HPLC system attached to a Waters Refractive Index Detector) at 420 nm in the presence of 0, 0.5 and 5 mM $H_2O_2$ solutions and 0, 0.5 and 5 mM AAPH solutions. The supernatant of the individual samples measured for the mass remaining studies were collected at each time point. Curcumin and CMA standards were used to quantify the concentration of curcumin and curcumin monoacrylate released.

Antioxidant Capacity of Released Degradation Products Over Time

A Trolox Equivalent Antioxidant Capacity (TEAC) assay was used to measure the total antioxidant activity of the degradation products after being released from the network in the presence of AAPH or $H_2O_2$. ABTS at 8 mg mL$^{-1}$ and APS at 1.32 mg mL$^{-1}$ were reacted overnight in the dark to produce ABTS free radical cations. Samples of a trolox standard were added to the ABTS free radical cation working solution for 5 minutes and then directly read at 734 nm using a UV-visible spectrophotometer microplate reader. Trolox was used as the reference antioxidant to directly compare the sample's antioxidant capacity. These values were reported as the Trolox Equivalence Antioxidant Concentration (TEAC) (mM). TEAC assays were completed at room temperature to inhibit any increase in free radical generation present in solution from thermal decomposition of AAPH throughout the duration of the assay.

Statistical Analysis

Significance testing was performed using a standard paired t-test with a significance threshold of $p<0.05$. The error bars in FIGS. 8 through 15 are reported as mean±standard error (n=3).

Results and Discussion

Bulk Film Synthesis and Characterization

Curcumin was converted to the CMA monomer by an acid-chloride alcohol esterification reaction as seen by Wattamwar et al. 14 By converting the hydroxyl groups to acrylates, the polyphenolic compound was incorporated into the backbone of a crosslinked network. Four different compositions of PBAE crosslinked networks (Table 4) were synthesized by reacting CMA (hydrophobic monomer) and PEG(400)DA (hydrophilic monomer) with a primary diamine crosslinker, TTD at a ratio of total acrylate to amine protons (RTAAP) of 1.0. TTD, acting as a Michael donor, reacted with the alkene groups present on either acrylate to form PBAE bonds. The four amine proton reaction sites on the primary diamine allow for a crosslinked network to proceed. The films were then washed with anhydrous acetonitrile to remove any unreacted monomers and dried under vacuum. The primary diamine and multiacrylate chemistry results in a bulk polymeric material with degradable beta-amino ester linkages. Under neutral conditions in a buffered solution, the primary mechanism of network degradation is base-catalyzed hydrolysis at the ester bond initiated by water. This allows for controlled release of active curcumin dependent on the CMA content of the network.

Figure 8A:
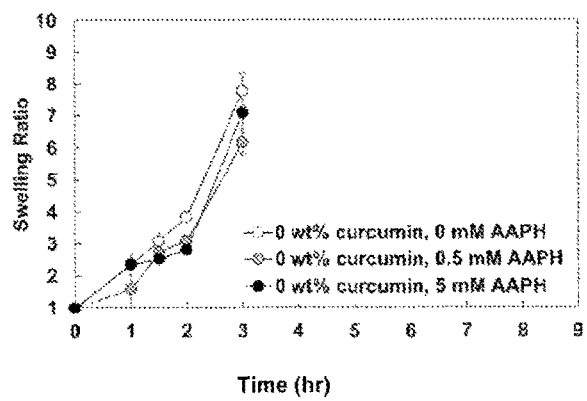
FIG. 8 shows swelling ratio profiles of 0 wt % (FIG. 8A), 10 wt % (FIG. 8B), 26 wt % (FIG. 8C), and 32 wt % (FIG. 8D) curcumin conjugated PBAE films in the presence of 0, 0.5 and 5 mM AAPH solutions. (Mean±SEM, n=3).
Figure 8B:
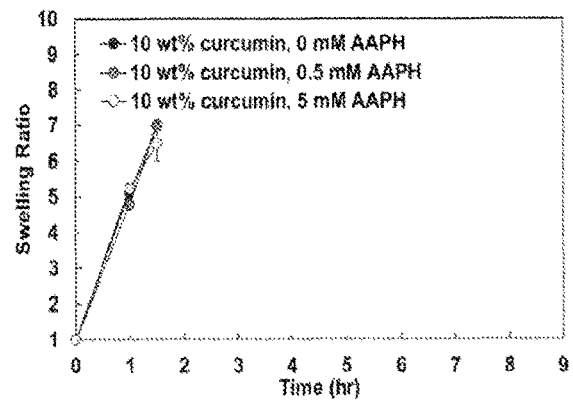
Figure 8C:
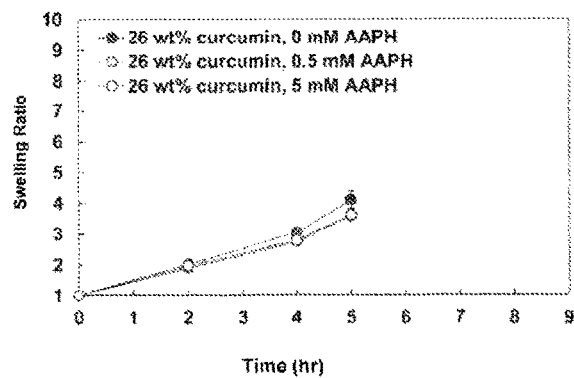
Figure 9:
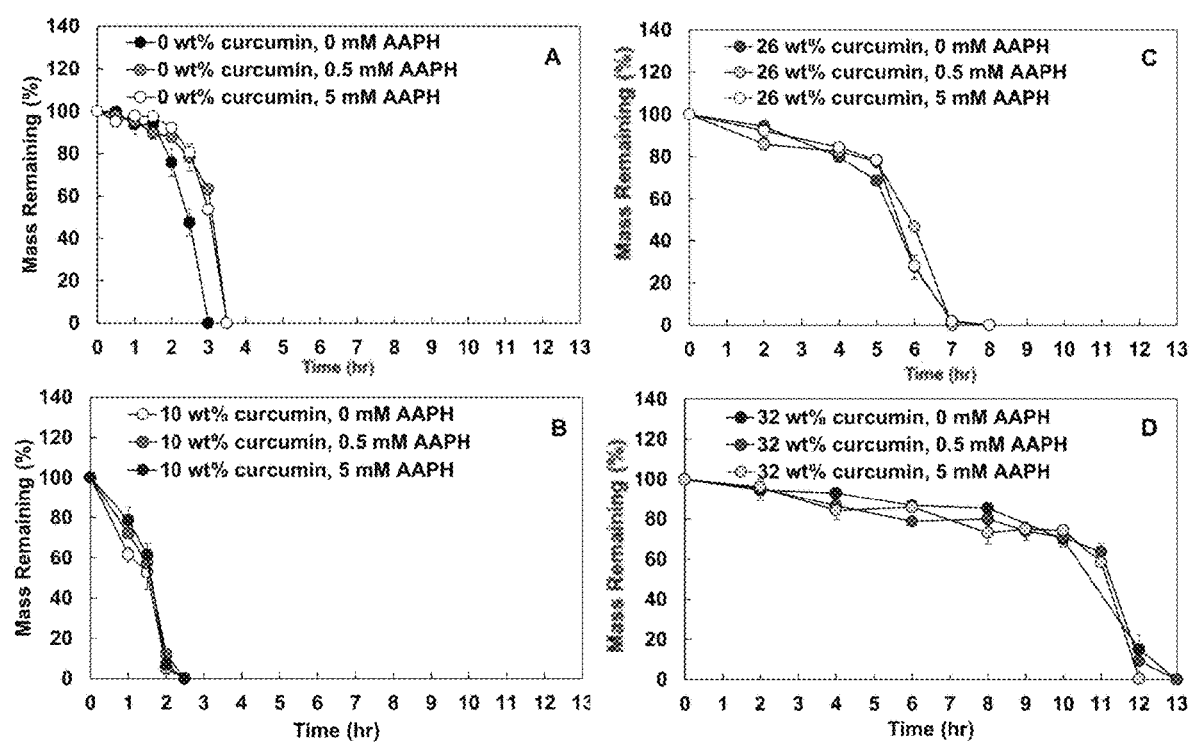
FIG. 9 shows mass remaining profiles of 0 wt % (FIG. 9A), 10 wt % (FIG. 9B), 26 wt % (FIG. 9C), and 32 wt % (FIG. 9D) curcumin conjugated PBAE films in the presence of 0, 0.5 and 5 mM AAPH solutions. (Mean±SEM, n=3).
Figure 10:
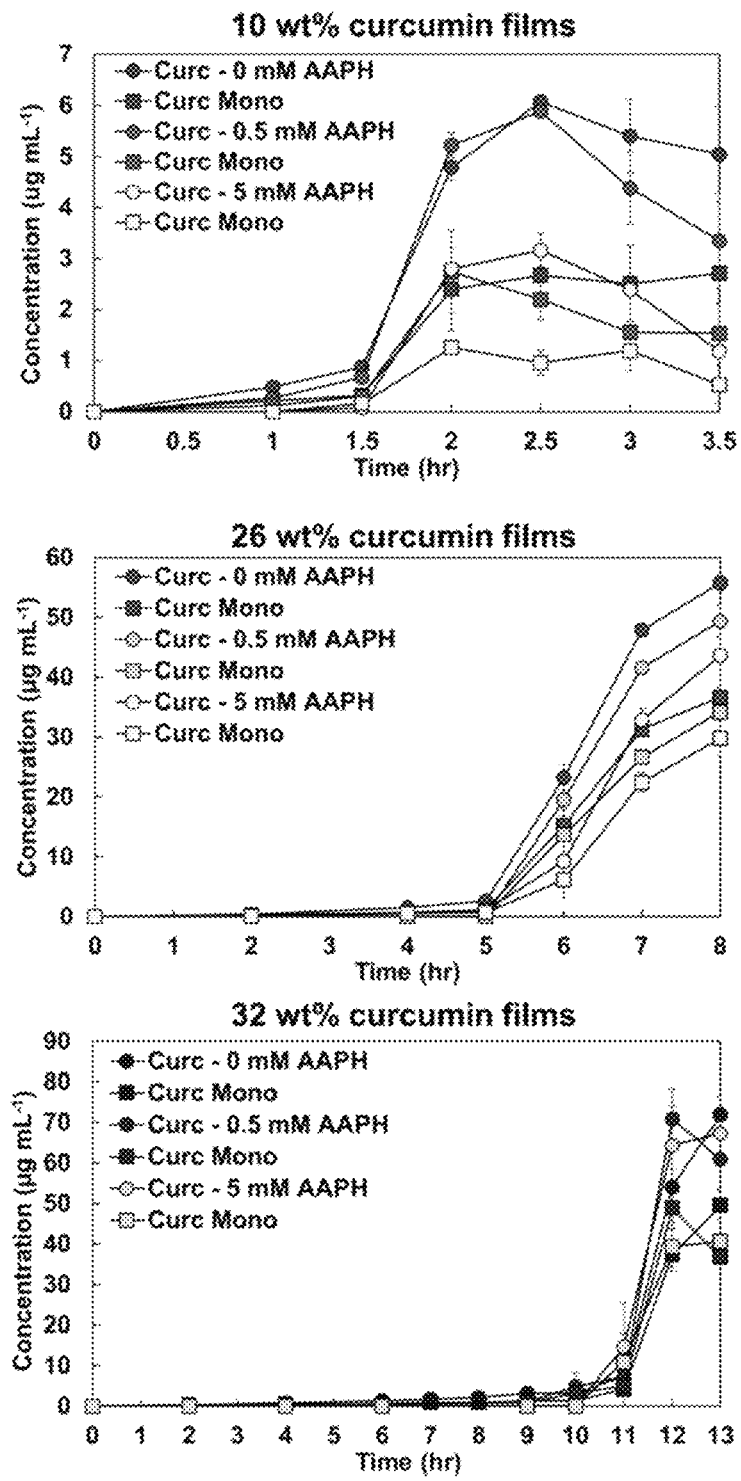
FIG. 10 shows curcumin release product profiles from 10 wt %, 26 wt %, and 32 wt % curcumin conjugated PBAE films in the presence of 0, 0.5 and 5 mM AAPH solutions. (Mean±SEM, n=3).
Figure 11:
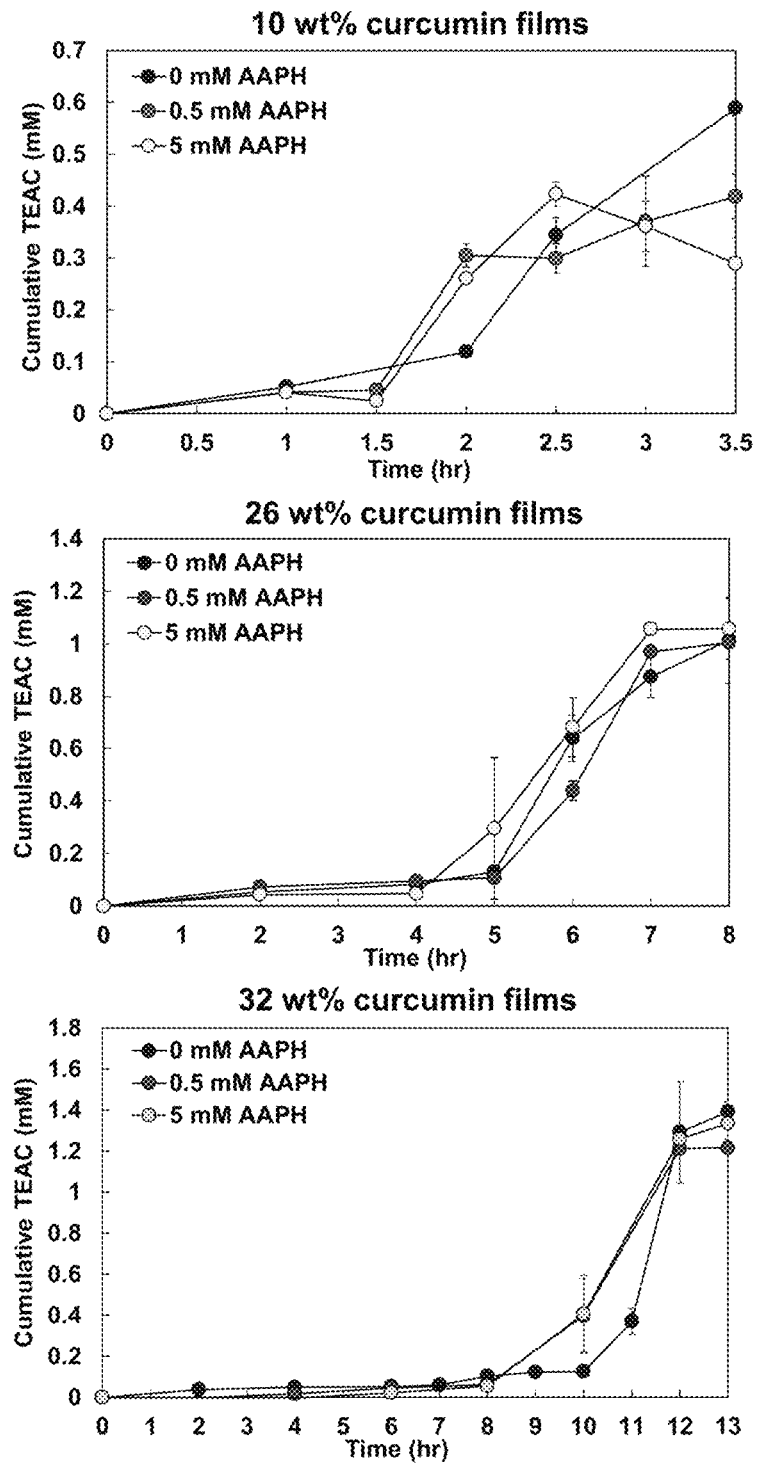
FIG. 11 shows the cumulative trolox equivalence antioxidant concentration (TEAC, mM) of 10, 26, and 32 wt % curcumin conjugated PBAE films in the presence of 0, 0.5, 5 mM AAPH solutions. (Mean±SEM, n=3).

Bulk films of 0-32 wt % loaded curcumin were evaluated to determine correlation of swelling, polymer degradation, and release in oxidative solutions to antioxidant loading. In neutral environments (0.1% (w/v) Tween 80 PBS, pH 7.4), the maximum swelling ratios over time decreased with increase in relative hydrophobicity of the network, ultimately extending the degradation times as well. The swelling ratios (FIG. 8 and FIG. 12) and total polymer content (FIG. 9 and FIG. 13) over time of four different film compositions were obtained in a control 0.1% (w/v) Tween 80 PBS (pH 7.4) environment. In the absence of oxidizing environments, the 0, 10, 26, and 32 wt % curcumin conjugated films degraded in 3, 2.5, 8, and 13 hours respectively. The rate of degradation time increased as the hydrophobicity of the network increased, although the integrity of the network appeared lower in the 10 wt % loaded curcumin film compared to the 0 wt % loaded curcumin film (FIGS. 9 and 10). The incorporation of PEG(400)DA and CMA into the network could change with respect to the reactivity of the two starting materials (PEG(400)DA and CMA) versus the reactivity of PEG(400)DA alone; therefore, the trend of diminished maximum swelling ratios and extended degradation times as the incorporation of CMA increases remains true for the curcumin conjugated systems.

AAPH Investigation

Swelling Profiles in the Presence of AAPH

The evaluation by which curcumin conjugated PBAE networks degrade in the presence of oxidative environments such as AAPH, an alkyl free radical generator, and $H_2O_2$, a reactive intermediate found in all cellular environments, gives insight to the effect that oxidative environments have on the polymeric network and the curcumin release products. AAPH solutions had no substantial effect on the swelling profiles of the four different networks investigated. In 0.1% A (w/v) Tween 80 PBS (pH 7.4), films that had no curcumin conjugated into the network (FIG. 8A) had increased water uptake compared to curcumin-conjugated films due to extent of hydrophilicity and swelled 7.09±1.3 times its original mass over 3 hours before losing integrity. In the presence of 0.5 and 5 mM AAPH, the swelling ratios over time increased to 6.17±0.53 and 7.77±0.46 times its original mass, losing integrity at 3 hours as well. The equilibrium swelling ratios were not statistically different ($p>0.05$). For 10 wt % curcumin loaded films (FIG. 8B), the observed maximum swelling ratios of the films in 0, 0.5 and 5 mM AAPH were 6.98±0.15, 6.98±0.27, and 6.48±0.50 over 1.5 hours. The swelling decreased and time before integrity was lost increased as the hydrophobicity of the network increased. This was due to higher incorporation of CMA, a more hydrophobic molecule than PEG(400)DA. 26 wt % curcumin films swelled over 5 hours before losing integrity with a maximum swelling ratio of 4.09±0.29 in with the absence of a free radical generator (FIG. 8C). Films in the presence of 0.5 and 5 mM AAPH swelled at similar rates over 5 hours until the last point of integrity, where the maximum swelling ratios are slightly lower but within error at 3.5±0.04 and 3.6±0.16 respectively.

Figure 8D:
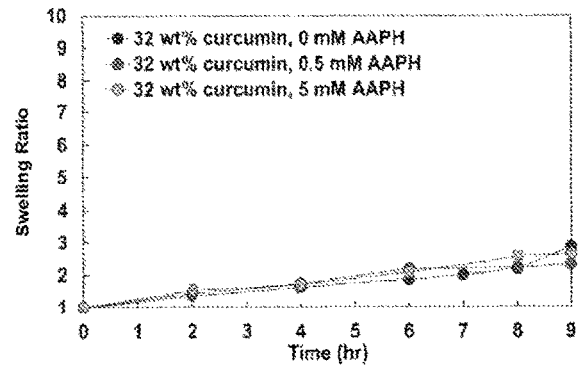

Similarly, there was no significant effect on the swelling profiles of the 32 wt % curcumin film in 0, 0.5 and 5 mM AAPH solution (FIG. 8D). The maximum swelling ratios were 2.8±0.16, 2.6±0.036, 2.3±0.13 respectively and the integrity of all three films was lost over 9 hours. Regarding both AAPH solutions of interest, AAPH has no effect on the integrity of the network or the degree of swelling compared to the control solution.

Total Polymer Content in the Presence of AAPH

The mass of the total polymer content of the curcumin conjugated PBAE films was investigated to observe the degradation of the films present in the presence of AAPH. The time at which 50% of the polymer mass remained was calculated (MT50) for each composition in each solution. For AAPH, a slight shift in the MT50 values was observed in the presence of AAPH (Table 5). There was an increase in MT50 for 0 wt % curcumin films and 32 wt % curcumin films in 0.5 and 5 mM AAPH, where the rest of curcumin conjugated films shift to the left. Significant change in the MT50 value was compared to the control using a paired t-test. The 0 wt % curcumin film's MT50 in the 0.5 mM AAPH solution was 5.4 minutes slower than the control ($p<0.05$) and the MT50 value in 5 mM AAPH was 14.4 minutes slower compared to the control ($p<0.05$). The 10 wt % film MT50 value shifted less than 30 minutes in the presence of each solution when compared to the control film ($p>0.05$), and a 20-minute change was seen for the 26 wt % films when compared in 5 mM AAPH ($p>0.05$). The final degradation time of each film formulation did not change when degraded in either 0.1% Tween 80 PBS, 0.5, or 5 mM AAPH solutions (FIG. 9). AAPH solution did not appear to have a significant effect on the total polymer content remaining throughout the degradation study as the rate of degradation of the polymer containing no curcumin was rapid in the control solution.

TABLE 5

Comparison of time at which 50% mass of the polymer remains in the control, 0.5, and 5 mM AAPH and $H_2O_2$ solutions

| | | MT50 (hr) Film Composition (wt % curcumin) | | | |
| --- | --- | --- | --- | --- | --- |
| Solution | Concentration (mM) | 0 | 10 | 26 | 32 |
| 0.1 (w/v) % PBS (pH 7.4) | — | 2.45 | 2.04 | 5.89 | 10.7 |
| AAPH (pH 7.4) | 0.5 | 3.10 | 1.60 | 5.80 | 11.2 |
| | 5 | 3.00 | 1.58 | 5.56 | 11.1 |
| $H_2O_2$ (pH 7.4) | 0.5 | 1.89 | 1.56 | 4.71 | 6.41 |
| | 5 | 1.76 | 1.35 | 2.02 | 3.06 |

Release Profiles in the Presence of AAPH

Curcumin PBAE films were submerged in 0.5 and 5 mM AAPH solutions, samples were collected periodically over time, and the release products were analyzed via HPLC coupled with UV-visible detector and evaluated at 420 nm. In FIG. 10, the release profiles of three different compositions are plotted in a control solution (0.1% (w/v) Tween 80 PBS, pH 7.4), 0.5 and 5 mM AAPH. The two active release products are curcumin and curcumin monoacrylate, verified by standards analyzed by HPLC. Within the 10 wt % curcumin film, curcumin was fully released from the network after 2.5 hours at 6 µg mL$^{-1}$ curcumin concentration, and 3 µg mL$^{-1}$ curcumin monoacrylate. The same samples were collected over time in the presence of the free radical generator AAPH. The films released over the same 2.5-hour period; however, after the curcumin was fully released, a decrease in concentration was seen for all products due to the AAPH induced oxidation of the active products. This phenomenon was even more pronounced in the presence of 5 mM AAPH, where the recovery of the curcumin concentration was only 3 µg mL$^{-1}$ and 1.23 µg mL$^{-1}$ for curcumin monoacrylate.

For the 26 wt % curcumin films over 8 hours, 55 µg mL$^{-1}$ curcumin and 34 µg mL$^{-1}$ curcumin monoacrylate was released. These degradation studies were repeated in the presence of AAPH, and similar to the 10 wt % films, the recovery of the degradation product was lower over time from the instantaneous consumption of curcumin as it is hydrolyzed and released into solution. The recovery appeared to be lower, but the rate of release was proportional, showing no notable change in release time other than consumption of the active component. The change in recovery was observable due to the controlled rate of release, allowing for more free radicals to generate within the system before curcumin is hydrolyzed into solution.

32 wt % curcumin films in release profiles showed a noteworthy change in release in the presence of AAPH, recovering 60.5 µg mL$^{-1}$ curcumin and 36.8 µg mL$^{-1}$ in the control environment, where in the 0.5 and 5 mM AAPH, the peak concentration of curcumin and curcumin monoacrylate was hour 12 rather than 13 (FIG. 10D). Comparing this to the slight increase in degradation time from FIG. 9D, a slight effect on the rate of hydrolysis in the presence of high concentrations of AAPH is observed, where curcumin incorporation is highest. The concentration of the free radicals in solution is able to accumulate in solution before the 32 wt % network fully loses its integrity. Because of this delayed release, the small concentration of curcumin released before hours 12 and 13 is consumed, so the overall recovery is lower at the final release time point; however, there is no significant impact on antioxidant capacity seen in FIG. 11.

Overall, the release studies in the control solution and the AAPH solution have similar release profiles and release products. Within each curcumin conjugated system, the release product contains both curcumin and curcumin monoacrylate. The curcumin monoacrylate release product could be due to incomplete conversion of curcumin triacrylate from the CMA mixture into the network, resulting in curcumin monoacrylate present in the release products. Throughout all the curcumin systems released in 0.5 and 5 mM AAPH, there is a decrease in recovery of the release product concentration over time. The decrease observed is due to the destabilization of curcumin as oxidation occurs in the presence of the alkyl radicals formed as AAPH thermally decomposes over time.

Antioxidant Capacity of Released Degradation Products Over Time in the Presence of AAPH The antioxidant capacity of the supernatant of the degradation products was measured using a TEAC assay. The concentration of the active antioxidant in a solution was reported as the theoretical equivalent concentration to that of the reference antioxidant, trolox. The 10 wt % curcumin film degradation products appeared less stable from both the release profiles (FIG. 10) and the TEAC assay profiles (FIG. 11) and began to lose activity after the films were fully degraded compared to the control solution (0.1% (w/v) Tween 80 PBS, pH 7.4). Interestingly, there was no observable change in antioxidant capacity of the curcumin release products from the 26 wt % film into the solution with a free radical generator. This could be due to the low concentration of free radicals present over time. If the release was at a lower concentration, or the free radical concentration was increased, an effect on the antioxidant capacity could potentially be seen.

The 32 wt % curcumin film cumulative TEAC profile (FIG. 11) was similar to the cumulative release profile seen in FIG. 10. There was an increase in antioxidant activity at 9 hours, where the integrity of the film was lost and the curcumin began to hydrolyze and release from the network; however, there was no significant change in the TEAC values at the final degradation times points of 12-13 hours, where release profiles show decay in absorbance.

$H_2O_2$ Investigation

Figure 12:
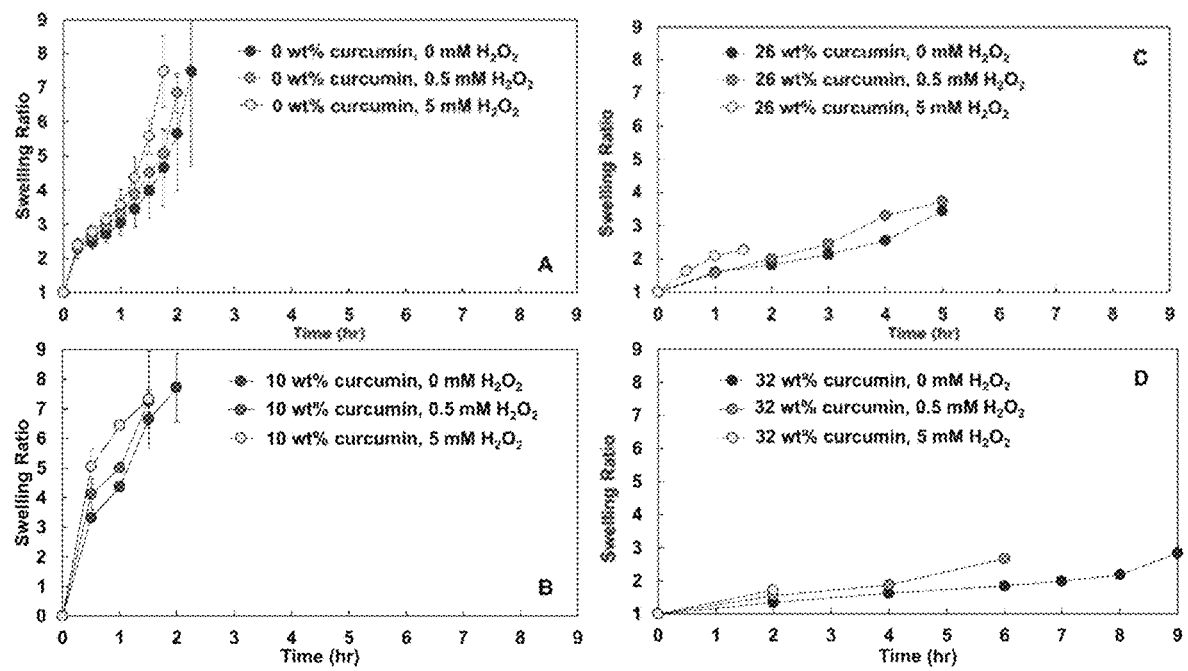
FIG. 12 shows swelling ratio profiles of 0 wt % (FIG. 12A), 10 wt % (FIG. 12B), 26 wt % (FIG. 12C), and 32 wt % (FIG. 12D) curcumin conjugated PBAE films in the presence of 0, 0.5 and 5 mM $H_2O_2$ solutions. (Mean±SEM, n=3).

Swelling Profiles in the Presence of $H_2O_2$ $H_2O_2$ solutions had a substantially greater impact on the swelling compared to AAPH. The same compositions of films were investigated in the presence of 0, 0.5 and 5 mM $H_2O_2$ in 0.1% (w/v) Tween 80 PBS (pH 7.4) (FIG. 12). Between each composition of film, $H_2O_2$ solutions decreased the time in which the films swelled and the time in which the film's integrity was lost. 0 wt % curcumin in a control 0.1% (w/v) Tween 80 PBS (pH 7.4) solution swelled over 2.5 hours, until integrity was lost. In the presence of 0.5 and 5 mM $H_2O_2$, the maximum swelling ratio was not affected, but the point of integrity decreased to 2 and 1.5 hours respectively (FIG. 12A).

10 wt % curcumin films had a different swelling response, where the rate of swelling in the presence of 5 mM $H_2O_2$ was significant, although the maximum swelling rate was still only 30 minutes faster than the control film in a normal solution (FIG. 12B). Interestingly, as the loading of curcumin increased within the film, the sensitivity of the film response appeared to change significantly. The swelling of 26 wt % films in the presence of $H_2O_2$ increased over 5 hours but appeared to maintain integrity throughout all 5 hours, similar to the control film; however, the swelling ratio tapers off between 4 and 5 hours, rather than continuing to swell. (FIG. 12C). Similarly, a significant difference was seen in swelling profiles in 32 wt % curcumin films, where the point of integrity was lost after 6 hours compared to 9 hours in a 0.5 mM $H_2O_2$ solution, and after 2 hours in a 5 mM $H_2O_2$ (FIG. 12D). The bulk films exposed to 0.5 and 5 mM $H_2O_2$ solutions responded with accelerated loss of integrity and a tapering effect on the swelling ratio values over time. This tapering effect could point to bulk erosion, where degradation of the polymer occurs directly at the surface rather than within the network. Specifically, this effect was seen on the 26 wt % curcumin bulk films in 5 mM $H_2O_2$, where the films swell for the first 1.5 hours, but the maximum swelling rate plateaued rather than continued to swell to the point of lost integrity. This observation could be the mechanism of peroxide mediated hydrolysis out-competing the rate of swelling.

Note the maximum swelling ratio decreased in the presence of $H_2O_2$ solutions as well. In the presence of $H_2O_2$, the rate of hydrolysis appeared to be more selective than the rate of swelling, and this sensitivity increased with higher incorporation of curcumin in to the network.

Total Polymer Content in the Presence of $H_2O_2$

Figure 13:
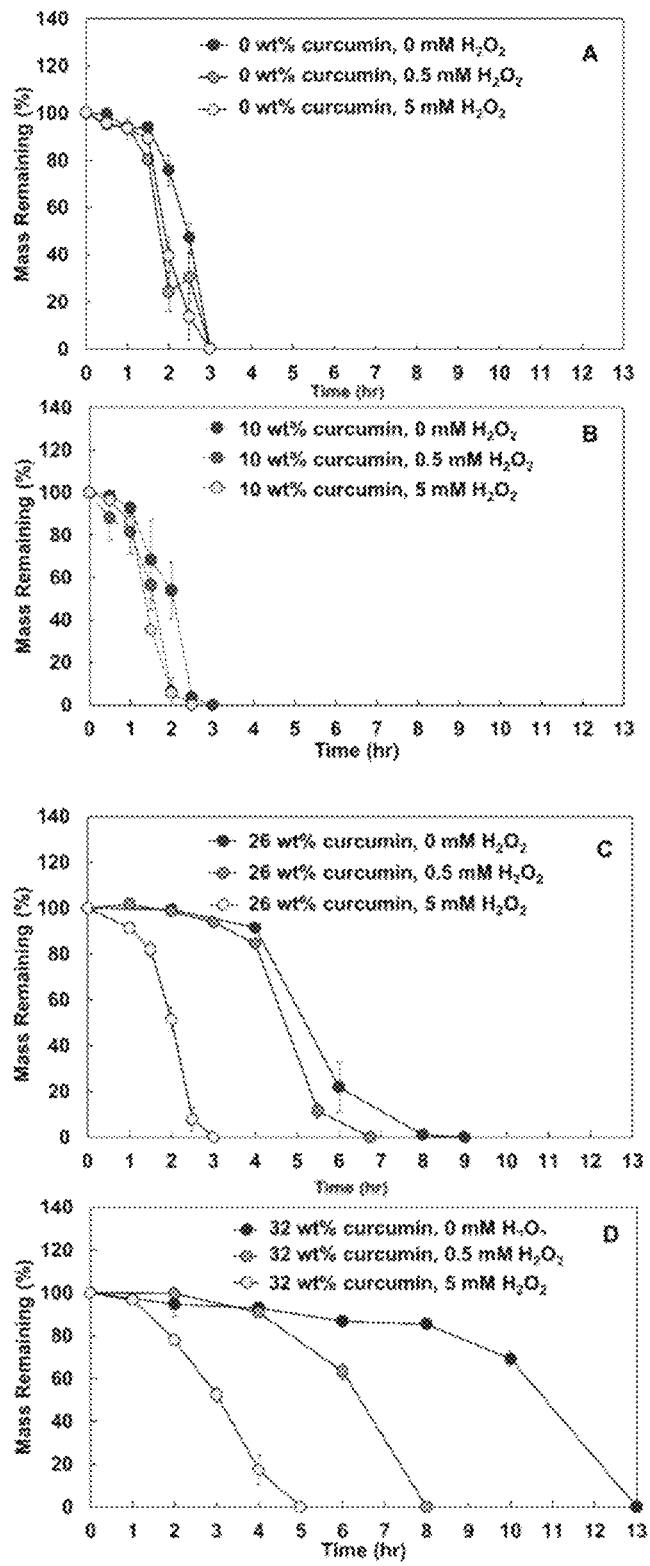
FIG. 13 shows mass remaining profiles of 0 wt % (FIG. 13A), 10 wt % (FIG. 13B), 26 wt % (FIG. 13C), and 32 wt % (FIG. 13D) curcumin conjugated PBAE films in the presence of 0, 0.5 and 5 mM $H_2O_2$ solutions. (Mean±SEM, n=3).

The films conjugated with curcumin dramatically decreased in total polymer mass remaining over time due to accelerated degradation in $H_2O_2$ (Table 5). Observing each curcumin conjugated film, increasing the $H_2O_2$ in solution decreased the MT50 value significantly, and accelerated degradation was enhanced upon the increase of the weight percent of curcumin (FIG. 13). The 32 wt % film had the largest change in MT50, where the MT50 in the control PBS solution was 10.7 hours and in 5 mM $H_2O_2$, the MT50 was 3.10 hours. The most significant $H_2O_2$ response on polymer degradation was 20× greater than polymer response to AAPH. The MT50 values of the films in the presence of 0, 0.5 and 5 mM AAPH, and $H_2O_2$ are provided for direct comparison in Table 5. The presence of $H_2O_2$ enhances hydrolysis of the network impressively and accelerates polymer degradation. While homeostatic systems obtain 10-100 μM levels of $H_2O_2$ present at one time, oxidative stress is promoted in concentrations>1000 μM.26 The PBAE systems are responsive to concentrations of peroxide that could potentially be found in majorly compromised states in the body, showing the potential for true impact in physiological environments. The films that were comprised of only PEG(400)DA appeared to be the least affected by $H_2O_2$. A potential reason for enhanced sensitivity could be due to a shift in antioxidant-oxidant balance in solution, urging the release of curcumin to neutralize the system.

Release Profiles in the Presence of $H_2O_2$

Figure 14:
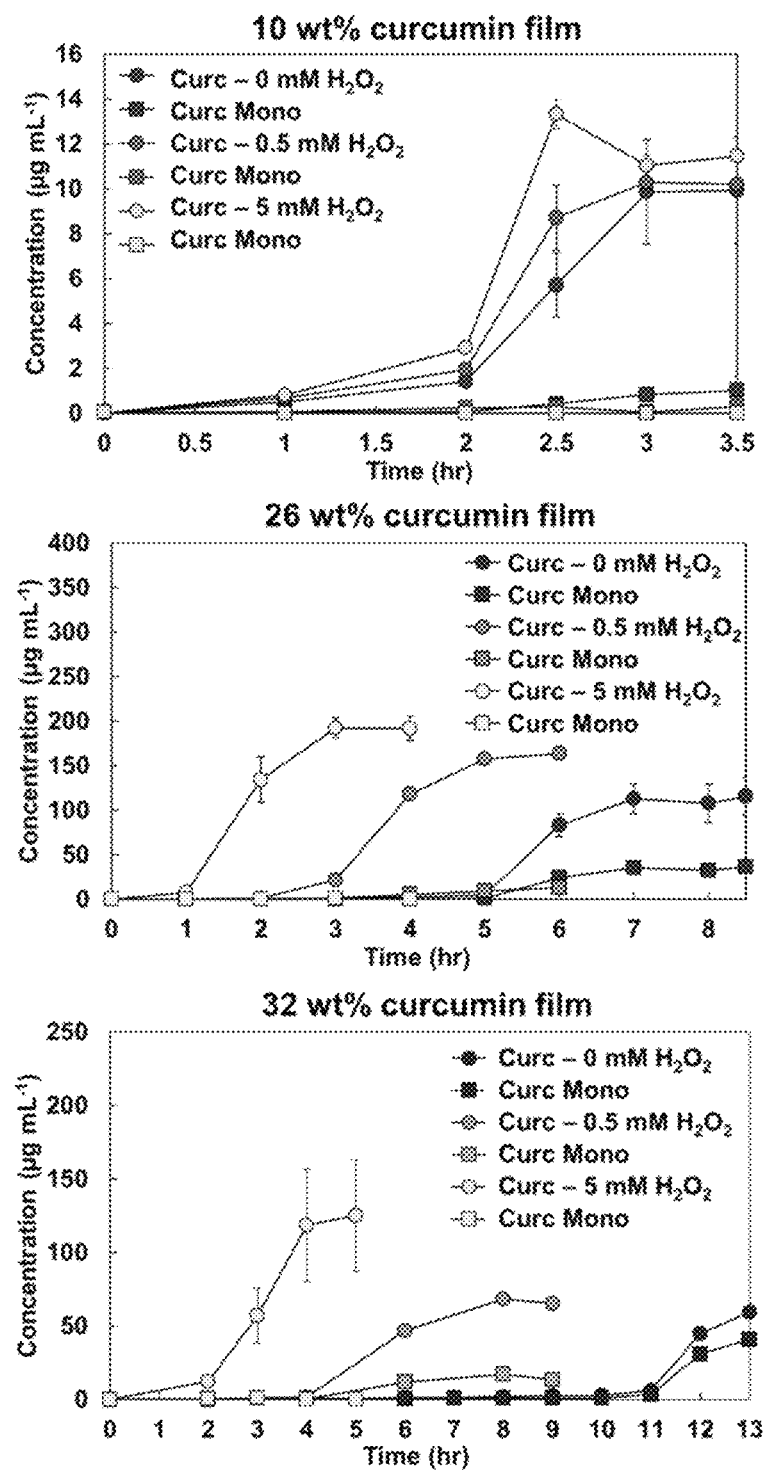
FIG. 14 shows curcumin release product profiles from 10 wt %, 26 wt %, and 32 wt % curcumin conjugated PBAE films in the presence of 0, 0.5 and 5 mM H2O2 solutions. (Mean±SEM, n=3).

The release profiles of the three curcumin-conjugated films in the presence of 0, 0.5, and 5 mM $H_2O_2$ are shown in FIG. 14. 26 wt % curcumin films were punched from a film (n=3 for each treatment solution) and the release products, curcumin and curcumin monoacrylate, were observed by collecting supernatant over the 8-hour release period. 26 wt % curcumin films in 0.1% (w/v) Tween 80 PBS (pH 7.4) did not release a significant amount of curcumin until hour 6. Comparing this value to the swelling profile, this was 1 hour after films lose integrity. The final recovery concentration of curcumin and curcumin monoacrylate is 115.5±21.7 and 36.3±6.8 μg mL$^{-1}$ respectively. Surprisingly, in the presence of 0.5 mM $H_2O_2$, the concentration of curcumin monoacrylate decreased to 12.9±4.9 μg mL$^{-1}$ and curcumin increased to 163.5±6.7 μg mL$^{-1}$ as full degradation was accelerated to 6 hours. With 10-fold increase in $H_2O_2$ concentration, the curcumin monoacrylate was completely removed from solution and 191.7±13.7 μg mL$^{-1}$ curcumin was recovered after 4 hours. Not only was the hydrolysis within the network sensitive to $H_2O_2$, but the acrylate group on the curcumin monoacrylate degradation product hydrolyzes, recovering only free curcumin at 5 mM $H_2O_2$. The sensitivity of hydrolysis appeared dependent upon the amount of curcumin conjugated to the network.

At 0.5 mM $H_2O_2$, 26 wt % curcumin films degraded 33% faster than in the control PBS solution, where 32 wt % curcumin films degraded 62.5% faster than in the control PBS solution and 10 wt % curcumin films had no change in total degradation time. In 5 mM $H_2O_2$, 26 wt % curcumin films degradation time increased by 100% than the control solution, where the shift in degradation significantly increased to 160% faster when curcumin is responsible for 32% of the total weight of the polymer.

The most noteworthy effect can be seen in the release profile (FIG. 14), where the $H_2O_2$ does not only mediate accelerated degradation of the polymer, but also promotes release of 100% curcumin by converting all release products into free curcumin. This phenomenon can be due to the synergistic effect of the peroxide and amino degradation groups present in solution, allowing for enhanced degradation of the polymer network with recovery of curcumin and triggered degradation of the network. This not only releases curcumin back into its active state, but also increases the antioxidant capacity of the overall solution. This discovery of mediated release that is dependent on curcumin loading and concentration of $H_2O_2$ defines a new mechanism by which curcumin conjugated degradable PBAE systems can be controlled for proper therapeutic delivery.

Figure 15:
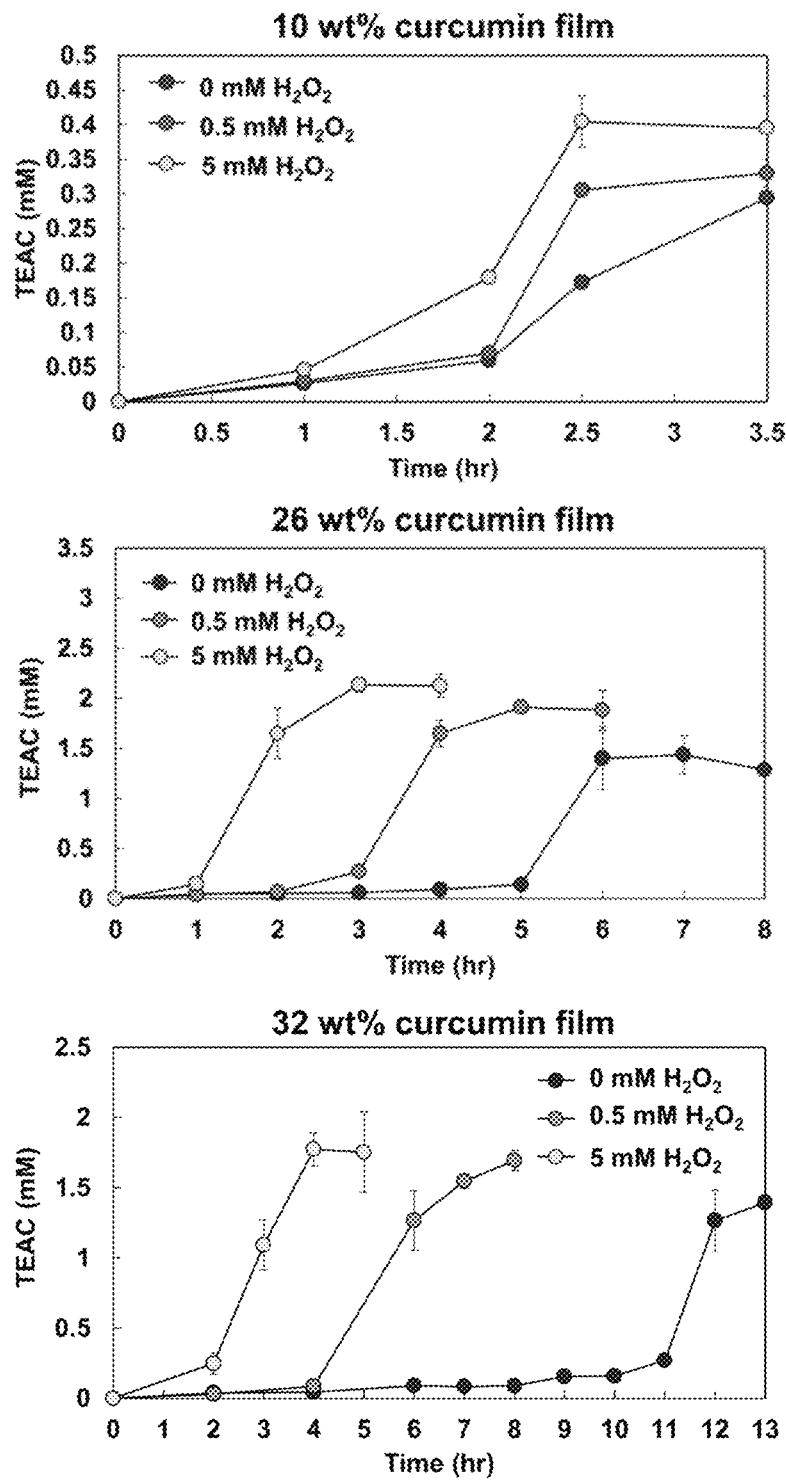
FIG. 15 shows cumulative Trolox equivalence antioxidant concentrations (TEAC, mM) over time of 10, 26, and 32 wt % curcumin conjugate PBAE films in the presence of 0, 0.5, 5 mM $H_2O_2$. (Mean±SEM, n=3).

Antioxidant Capacity of Released Degradation Products Over Time in the Presence of $H_2O_2$ The antioxidant capacity of the release products into solution were investigated after being exposed to the $H_2O_2$. At 0.5 mM $H_2O_2$, the activity profile mimics the release curve profile (FIG. 15). As active curcumin is released into solution, the equivalent antioxidant capacity, using Trolox as an antioxidant reference compound, increased as well, showing active products accumulating in the environment as the network degrades. There was a slight increase in the antioxidant potential for all three film compositions when degraded in 0.5 and 5 mM $H_2O_2$. This increase is correlated with the release of free curcumin compared to the curcumin release derivative curcumin monoacrylate into the system, which is hypothesized to be classified with lower activity due to its lower susceptibility to consumption in the presence of AAPH as seen in Jordan et al.25

Conclusions $H_2O_2$ mediated release of curcumin from curcumin conjugated PBAE systems were reported, showing enhanced sensitivity with higher incorporation of curcumin into the network. This showcase of accelerated release introduces an exciting self-regulating property of curcumin conjugated PBAE drug delivery systems that was previously unknown. Interestingly, not all oxidizing environments had the same effect on the hydrolysis of the crosslinked network. Although the alkyl and peroxyl radicals had a higher affinity to consume the curcumin release products from the polymer, the $H_2O_2$ aided in accelerated polymer degradation. Not only was curcumin released at a faster rate, the acrylate found on curcumin monoacrylate was further hydrolyzed, enhancing the release of free active curcumin.

This discovery illustrates the use of tunable drug delivery properties to provide proper therapeutic doses in abnormal environments and the discovery of an exciting stimulated mechanism of release of curcumin. Further investigation will continue to understand effects of pulsatile release to look at the effects of the polymer degradation when exposed to abnormal concentrations of $H_2O_2$ and then back into a neutral environment. This interesting concept will help to modify the monomer selection pending the environment balance required for homeostatic environments and will be able to be used in diseased environments known for burst release concentration of ROS.

What is claimed is:

1. A method of delivering a curcuminoid to a body tissue, the method comprising:
    a) obtaining or having obtained a delivery composition comprising microparticles comprising a polymer, the polymer comprising a plurality of monomeric portions each comprising the curcuminoid interposed by two acrylate-containing moieties each conjugated to a poly(beta-amino ester), the poly(beta-amino ester) comprising a diamine crosslinker linked to a poly(ethylene glycol) diacrylate having a molecular weight of 400 Da (PEG(400) diacrylate), wherein the ratio of the total number of acrylate groups in the acrylate-containing moieties and in the PEG(400) diacrylate to the amine protons of the diamine crosslinker is from about 1:1 to about 1:3; and
    b) exposing the delivery composition to an amount of hydrogen peroxide as a trigger, thereby triggering an accelerated release of the curcuminoid to the body tissue as compared to release of the curcuminoid in the absence of the trigger.

2. The method of claim 1, wherein the the accelerated release is characterized by release of the curcuminoid from the delivery composition in proportion to the amount of the hydrogen peroxide.

3. The method of claim 1, wherein the amount of hydrogen peroxide is a concentration of up to about 5 mM.

4. The method of claim 1, wherein the amount of hydrogen peroxide is from about 0.5 mM to about 5 mM of hydrogen peroxide.

5. The method of claim 1, wherein the diamine crosslinker is a primary diamine molecule.

6. The method of claim 1, wherein the ratio of the total number of acrylate groups in the acrylate-containing moieties and in the PEG(400) diacrylate to the amine protons of the diamine crosslinker is about 1:1.

7. The method of claim 1, wherein the curcuminoid is selected from the group consisting of curcumin, demethoxycurcumin, demethoxycurcumin, and any combination thereof.

8. The method of claim 1, wherein the microparticles are formed from a biodegradable film of the polymer.

9. A system for delivering a curcuminoid to a body tissue, the system comprising:
   a) a delivery composition comprising microparticles comprising a polymer;
   wherein the polymer comprises a plurality of monomeric portions each comprising curcuminoid interposed by two acrylate-containing moieties;
   and wherein each of the two acrylate-containing moieties is conjugated to a poly(beta-amino ester) comprising a diamine crosslinker crosslinked to a poly(ethylene glycol) diacrylate having a molecular weight of 400 Da (PEG(400) diacrylate),
   wherein the ratio of the total number of acrylate groups in the two acrylate-containing moieties and in the PEG (400) diacrylate to the amine portion of the diamine crosslinker is from about 1:1 to about 1:3; and
   b) an amount of hydrogen peroxide as a trigger;
   wherein upon exposure of the delivery composition to the trigger, the trigger reacts with the polymer of the delivery composition thereby allowing an accelerated release of the curcuminoid to the body tissue as compared to release of the curcuminoid in the absence of the trigger.

10. The system of claim 9, wherein the ratio of the total number of acrylate groups in the acrylate-containing moieties and in the PEG(400) diacrylate to the amine protons of the diamine crosslinker is about 1.

11. The system of claim 9, wherein the amount of hydrogen peroxide is from about 0.5 mM to about 5 mM.

12. The system of claim 9, wherein the accelerated release is characterized by release of the curcuminoid from the delivery composition in proportion to the amount of the hydrogen peroxide.

13. The system of claim 9, wherein the amount of hydrogen peroxide is at a concentration up to 5 mM.

14. The system of claim 9, wherein the diamine crosslinker is a primary diamine molecule.

15. The system of claim 9, wherein the curcuminoid is selected the group consisting of curcumin, demethoxycurcumin, bisdemethoxycurcumin, and any combination thereof.

16. The system of claim 9, wherein the microparticles are formed from a biodegradable film of the polymer.

17. A kit comprising the system of claim 9, wherein the curcuminoid and the trigger are provided in separate containers.

18. The kit of claim 17, wherein the microparticles are formed from a biodegradable film of the polymer.

19. The method of claim 1, wherein the curcuminoid is curcumin.

20. The kit of claim 17, wherein the amount of hydrogen peroxide is up to 5 mM.

21. The method of claim 1, wherein the microparticles comprise from about 26% wt/wt to about 32% wt/wt of curcuminoid.

* * * * *